United States Patent
David et al.

(10) Patent No.: US 7,077,873 B2
(45) Date of Patent: Jul. 18, 2006

(54) COMPOSITION FOR THE DYEING OF HUMAN KERATINOUS FIBRES COMPRISING A MONOCATIONIC MONOAZO DYE

(75) Inventors: Hervé David, Joinville le Pont (FR); Nathalie Berteuil, Brunoy (FR); Laurent Vidal, Paris (FR)

(73) Assignee: L'Oréal, SA, Paris (FR)

( * ) Notice: Subject to any disclaimer, the term of this patent is extended or adjusted under 35 U.S.C. 154(b) by 273 days.

(21) Appl. No.: 10/658,409

(22) Filed: Sep. 10, 2003

(65) Prior Publication Data

US 2004/0127692 A1 Jul. 1, 2004

Related U.S. Application Data

(60) Provisional application No. 60/410,311, filed on Sep. 13, 2002.

(30) Foreign Application Priority Data

Sep. 10, 2002 (FR) ............................. 02 11186

(51) Int. Cl.
*A61K 7/13* (2006.01)

(52) U.S. Cl. ............. 8/405; 8/407; 8/437; 8/451; 8/463; 8/466; 8/570; 8/571; 8/573; 8/574; 548/318.1; 548/321.1; 548/333.1; 548/400; 546/185; 546/193; 546/249

(58) Field of Classification Search ............. 8/405, 8/407, 437, 451, 463, 466, 570, 571, 573, 8/574; 548/318.1, 321, 333.1, 400; 546/185, 546/193, 249

See application file for complete search history.

(56) References Cited

U.S. PATENT DOCUMENTS

| | | | | |
|---|---|---|---|---|
| 3,578,387 | A | 5/1971 | Zviak et al. .................. | 8/10.1 |
| 4,003,699 | A | 1/1977 | Rose et al. ................... | 8/10.2 |
| 4,823,985 | A | 4/1989 | Grollier et al. ............... | 222/1 |
| 5,061,289 | A | 10/1991 | Clausen et al. ............... | 8/409 |
| 5,380,340 | A | 1/1995 | Neunhoeffer et al. ......... | 8/409 |
| 5,534,267 | A | 7/1996 | Neunhoeffer et al. ....... | 424/701 |
| 5,663,366 | A | 9/1997 | Neunhoeffer et al. .... | 548/371.4 |
| 5,708,151 | A | * 1/1998 | Mockli ...................... | 534/608 |
| 5,766,576 | A | 6/1998 | Lowe et al. ................. | 424/62 |
| 5,852,179 | A | 12/1998 | Dado ......................... | 534/581 |
| 5,980,587 | A | 11/1999 | Samain ....................... | 8/409 |
| 5,993,490 | A | 11/1999 | Rondeau et al. ............. | 8/426 |
| 6,099,592 | A | 8/2000 | Vidal et al. .................. | 8/409 |
| 6,099,593 | A | 8/2000 | Terranova et al. ........... | 8/409 |
| 6,284,003 | B1 | 9/2001 | Rose et al. .................. | 8/412 |
| 6,338,741 | B1 | 1/2002 | Vidal et al. .................. | 8/409 |
| 6,368,360 | B1 | 4/2002 | Samain ....................... | 8/426 |
| 6,645,258 | B1 | 11/2003 | Vidal et al. .................. | 8/405 |

FOREIGN PATENT DOCUMENTS

| | | |
|---|---|---|
| DE | 23 59 399 | 6/1975 |
| DE | 38 43 892 A1 | 6/1990 |
| DE | 41 33 957 A1 | 4/1993 |
| DE | 195 43 988 A1 | 5/1997 |
| DE | 197 21 619 A1 | 11/1998 |
| EP | 0 714 954 A2 | 6/1996 |
| EP | 0 770 375 A1 | 5/1997 |
| EP | 0 850 637 A1 | 7/1998 |
| FR | 1 584 965 | 2/1967 |
| FR | 2 586 913 | 3/1987 |
| FR | 2 733 749 | 11/1996 |
| FR | 2 741 798 A1 | 6/1997 |
| FR | 2 750 048 A1 | 12/1997 |
| GB | 1 026 978 | 4/1966 |
| GB | 1 153 196 | 5/1969 |
| JP | 53 95693 | 8/1978 |
| JP | 55 22638 | 2/1980 |
| JP | 2019576 | 1/1990 |
| JP | 05-163124 | 6/1993 |
| US | 63668 3601 | 9/1994 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 01/66646 | 9/2001 |

OTHER PUBLICATIONS

European Search Report for EP 03 29 2224, Examiner Van Bijlen, Jan. 12, 2004.
French Search Report for 02/11186, Examiner Van Bijien, Jun. 12, 2003.
English Language Derwent Abstract of FR 1 584 965.
English Language Derwent Abstract of DE 23 59 399.
English Language Derwent Abstract of JP 53 95693.
English Language Derwent Abstract of 55 22638.
English Language Derwent Abstract of FR 2 586 913.
English Language Derwent Abstract of DE 38 43 892 A1.
English Language Derwent Abstract of 05–163124.
English Language Derwent Abstract of WO 94/08969.
English Language Derwent Anstract of WO 94/08970.
English Language Derwent Abstract of WO 96/15765.
English Language Derwent Abstract of EP 0 714 954 A2.
English Language Derwent Abstract of FR 2 733 749.
English Language Derwent Abstract of EP 0 770 375 A1.
English Language Derwent Abstract of DE 195 43 988 A1.
English Langauge Derwent Abstract of FR 2 741 798 A1.
English Language Derwent Abstract of FR 2 750 048 A1.
English Language Derwent Abstract of EP 0 850 637 A1.
English Language Derwent Abstract of DE 197 21 619 A1.
English Language Derwent Abstract of JP 88 169 571.

* cited by examiner

*Primary Examiner*—Margaret Einsmann
*Assistant Examiner*—Eisa Elhilo
(74) *Attorney, Agent, or Firm*—Finnegan, Henderson, Farabow, Garrett & Dunner, L.L.P.

(57) ABSTRACT

A subject-matter of the disclosure is a novel composition for the dyeing of human keratinous fibres, for example, the hair, comprising a monocationic monoazo dye of formula (I) W1-N=N—W2-NW3-W4-W5, the dyeing processes employing it, the use of the dyes of formula (I) as direct dyes and the novel compounds of formula (I).

47 Claims, No Drawings

COMPOSITION FOR THE DYEING OF HUMAN KERATINOUS FIBRES COMPRISING A MONOCATIONIC MONOAZO DYE

This application claims benefit of U.S. Provisional Application No. 60/410,311, filed Sep. 13, 2002.

Disclosed herein is a novel composition for the dyeing of human keratinous fibres, such as the hair, comprising a specific monocationic monoazo dye, and the processes for dyeing fibres employing such a composition. Also disclosed herein are the novel monocationic monoazo dyes and the use of the dyes disclosed herein as direct dyes.

It is known to dye human keratinous fibres, such as the hair, with dyeing compositions comprising oxidation dye precursors, generally known as oxidation bases, such as ortho- or para-phenylenediamines, ortho- or para-aminophenols, and heterocyclic compounds. These oxidation bases are colourless or weakly coloured compounds that, in combination with oxidizing substances, give rise to coloured compounds by an oxidative coupling process.

It is also known that the hues obtained with these oxidation bases can be varied by combining them with couplers or colouring modifiers, the latter being chosen from, for example, aromatic meta-diamines, meta-aminophenols, meta-diphenols, and certain heterocyclic compounds, such as indole compounds.

The variety of the molecules employed as oxidation bases and couplers makes it possible to obtain a rich palette of colours.

An oxidation dyeing process comprises applying to the keratinous fibres oxidation bases, or a mixture of oxidation bases and couplers, with an oxidizing agent, for example an aqueous hydrogen peroxide solution, leaving to stand, and then rinsing the fibres. The colorations which result therefrom are permanent and powerful, and withstand external agents, for example light, bad weather, washing, perspiration, and rubbing. Generally applied at basic pH, they make it possible to obtain dyeing and, if desired, simultaneously, lightening of the fibre, which is reflected in practice by the possibility of obtaining a final coloration which is lighter than the original colour. In addition, lightening the fibre has the advantageous effect of producing a unified colour in the case of grey hair and, in the case of naturally pigmented hair, of making the colour emerge, that is to say of rendering it more visible.

It is also known to dye human keratinous fibres by direct dyeing. The process conventionally used in direct dyeing comprises applying to the fibres direct dyes, which are coloured, and colouring molecules having an affinity for the fibres, leaving to stand, and then rinsing the fibres.

It is known, for example, to use nitrobenzene, anthraquinone or nitropyridine direct dyes, azo, xanthene, acridine or azine dyes or triarylmethane dyes.

The colorations which result therefrom are particularly chromatic colorations which, however, are somewhat temporary or semipermanent. The nature of the interactions that bind the direct dyes to the fibre and their desorption from the surface and/or from the core of the fibre are responsible for their low dyeing power and for their poor resistance to washing or to perspiration. In addition, these direct dyes can be generally sensitive to light, because of the low resistance of the chromophore with regard to photochemical attacks, and may result over time in fading of the colouring of the hair. In addition, they can be sensitive to light, dependent on their distribution, (i.e., uniform or nonuniform), in the keratinous fibre.

It is known to use direct dyes in combination with oxidizing agents. However, direct dyes are generally sensitive to the action of oxidizing agents, such as aqueous hydrogen peroxide solution, and reducing agents, such as sodium bisulphite, which generally renders them difficult to use in compositions for lightening direct dyeing based on aqueous hydrogen peroxide solution and based on a basifying agent or in oxidation dyeing compositions in combination with oxidation dye precursors or couplers.

For example, provision has been made, in Patent Applications FR-1 584 965 and JP-062 711 435, to dye the hair with dyeing compositions based on direct nitro dyes and/or on disperse azodyes and on aqueous ammoniacal hydrogen peroxide solution by applying to the hair, a mixture of the said dyes and of the said oxidizing agent prepared immediately before use. However, the colorations obtained can be insufficiently persistent and disappear on shampooing, allowing the lightening of the hair fibre to become apparent. Such a coloration can become unattractive on changing over time.

Provision has also been made, in Patent Applications JP-53 95693 and JP 55 022638, to dye the hair with compositions based on cationic direct dyes of oxazine type and on aqueous ammoniacal hydrogen peroxide solution by applying, in a first stage, aqueous ammoniacal hydrogen peroxide solution and then, in a second stage, a composition based on the direct oxazine dye. This coloration may not be satisfactory because of the fact that it requires a process rendered excessively slow by the leave-in times of the two successive stages. Furthermore, if a mixture prepared at the time of use of the direct oxazine dye with aqueous ammoniacal hydrogen peroxide solution is applied to the hair, no coloration is produced or, at least, a coloration of the hair fibre is obtained which is virtually nonexistent.

More recently, Patent Application FR 2 741 798 has disclosed dyeing compositions comprising direct azo or azomethine dyes comprising at least one quaternized nitrogen atom, the said compositions having to be mixed at the time of use at basic pH with an oxidizing composition. These compositions make it possible to obtain colorations with homogeneous, persistent and bright highlights. However, they do not make it possible to dye human keratinous fibres, such as the hair, with as much power as with oxidation dyeing compositions.

Thus, there exists a real need to try to find chromatic direct dyes that make it possible to dye human keratinous fibres as powerfully as oxidation dyes, which can be as stable as oxidation dyes towards light, which can also be resistant to bad weather, washing and perspiration, and which, in addition, can be sufficiently stable in the presence of oxidizing and reducing agents to be able to simultaneously obtain lightening of the fibre, either by use of lightening direct compositions comprising them or by the use of oxidation dyeing compositions comprising them. There also exists a real need to try to find direct dyes that make it possible to dye human keratinous fibres in order to obtain a very broad range of colours, for example highly chromatic colours, without forgetting the "basic" shades, such as the blacks and the browns.

These aims can be achieved with the present disclosure, one aspect of which is a composition for the dyeing of human keratinous fibres, for example the hair, comprising, in a cosmetically acceptable medium, at least one monocationic monoazo dye of formula (I):

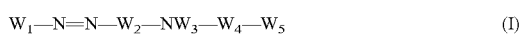

$$W_1-N=N-W_2-NW_3-W_4-W_5 \qquad (I)$$

wherein:
W$_1$ is chosen from 5- and 6-membered cationic aromatic heterocycles of formulae (II) and (III):

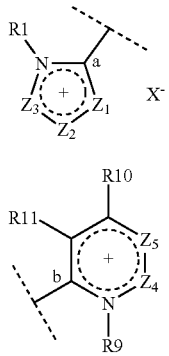

Formula (II)

Formula (III)

wherein:
- Z$_1$ is chosen from an oxygen atom, a sulphur atom, NR$_2$ radicals, and CR$_3$ radicals,
- Z$_2$ is chosen from a nitrogen atom and CR$_4$ radicals,
- Z$_3$ is chosen from an NR$_{12}$ radical and CR$_{13}$ radicals,
- Z$_4$ is chosen from a nitrogen atom and CR$_{14}$ radicals,
- Z$_5$ is chosen from a nitrogen atom and CR$_{15}$ radicals, with the proviso that formulae (II) and (III) do not comprise more than two adjacent heteroatoms;
- the bond a connects the 5-membered cationic ring of formula (II) to the azo functional group of formula (I),
- the bond b connects the 6-membered cationic ring of formula (III) to the azo functional group of formula (I),
- X$^-$ is chosen from organic and inorganic anions,
- W$_2$ and W$_4$ (formula I), which may be identical or different, are chosen from divalent carbonaceous aromatic groups and pyridine groups of formulae (IV) and (V):

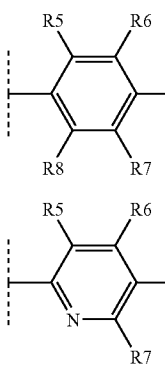

Formula (IV)

Formula (V)

W$_3$ is chosen from a hydrogen atom and C$_1$–C$_6$ alkyl radicals, which may be optionally substituted with at least one radical chosen from hydroxyl radicals, alkoxy radicals, amino radicals, mono(C$_1$–C$_4$)alkylamino radicals, and di(C$_1$–C$_4$)alkylamino radicals, W$_5$ is chosen from 5-membered nitrogenous heteroaromatic radicals connected to W$_4$ via the nitrogen atom of the ring of the said heteroaromatic radicals, the heteroaromatic radicals being chosen from pyrazolyl, pyrrolyl, imidazolyl, triazolyl and thiadiazolyl radicals, it being possible for each of these heteroaromatic radicals to be substituted with at least one entity chosen from hydrogen, chlorine, and fluorine atoms, C$_1$–C$_6$ alkyl radicals which may optionally be substituted by at least one radical chosen from hydroxyl, C$_1$–C$_4$ alkoxy, C$_2$–C$_4$ (poly)hydroxy-alkoxy, amino, (di)(C$_1$–C$_4$)alkylamino, C$_2$–C$_4$ (poly)hydroxyalkylamino, carboxyl, sulpho, C$_1$–C$_4$ alkoxycarbonyl and C$_1$–C$_4$ alkylthio radicals; or by at least one phenyl radical, which may optionally be substituted by at least one entity chosen from halogen atoms and hydroxyl, C$_1$–C$_2$ alkoxy, amino, (di)(C$_1$–C$_2$)alkylamino, carboxyl, sulpho, C$_1$–C$_4$ alkyl, and C$_1$–C$_2$ alkylthio radicals, R$_1$, R$_2$, R$_9$ and R$_{12}$, which may be identical or different, are chosen from phenyl radicals that may optionally be substituted or C$_1$–C$_8$ alkyl radicals, which may optionally be substituted with at least one radical chosen from hydroxyl, C$_1$–C$_2$ alkoxy, C$_2$–C$_4$ (poly)hydroxyalkoxy, amino, and (di)(C$_1$–C$_2$)alkylamino radicals, R$_5$, R$_6$, R$_7$ and R$_8$, which may be identical or different, are each chosen from a hydrogen atom; a chlorine atom; a bromine atom; linear and branched C$_1$–C$_8$ hydrocarbonaceous chains, which can form at least one 3- to 6-membered carbonaceous ring and which can be saturated or unsaturated, one or more carbon atoms of the carbonaceous chain of which can be replaced by at least one entity chosen from oxygen, nitrogen, and sulphur atoms and an SO$_2$ group, and the carbon atoms of which can, independently of one another, be substituted by at least one halogen atom; with the proviseo that R$_5$, R$_6$, R$_7$ and R$_8$ do not comprise a peroxide bond or a diazo or nitroso radical, R$_3$, R$_4$, R$_{10}$, R$_{11}$, R$_{13}$, R$_{14}$ and R$_{15}$, which may be identical or different, are chosen from a hydrogen atom and linear and branched C$_1$–C$_{16}$, for example C$_1$–C$_8$, hydrocarbonaceous chains which can form at least one 3- to 6-membered carbonaceous ring and which can be saturated or unsaturated, one or more carbon atoms of the carbonaceous chain of which can be replaced by at least one entity chosen from oxygen, nitrogen, and sulphur atoms and an SO$_2$ group, and the carbon atoms of which can, independently of one another, be substituted by at least one halogen atom; with the proviso that R$_3$, R$_4$, R$_{10}$, R$_{11}$, R$_{13}$, R$_{14}$ and R$_{15}$ do not comprise a peroxide bond or a diazo or nitroso radical, R$_4$ with R$_{13}$ and R$_{14}$ with R$_{15}$ can form a carbonaceous aromatic ring, such as a phenyl.

According to the present disclosure, when it is indicated that one or more of the carbon atoms of the hydrocarbonaceous chain defined for the R$_3$, R$_4$, R$_5$, R$_6$, R$_7$, R$_8$, R$_{10}$, R$_{11}$, R$_{13}$, R$_{14}$ and R$_{15}$ radicals can be replaced by an oxygen, nitrogen or sulphur atom or by an SO$_2$ group and/or that these hydrocarbonaceous chains are unsaturated, this means that it is possible, by way of example, to carry out the following conversions:

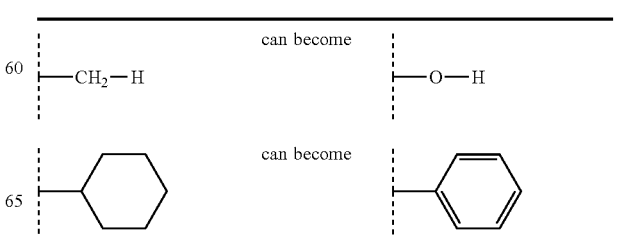

-continued

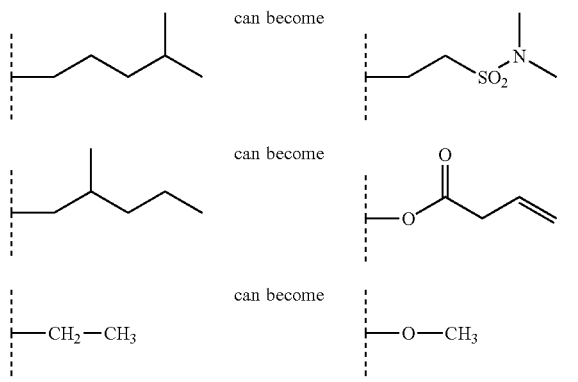

In the present disclosure, the term "branched hydrocarbonaceous chain" is understood to mean a chain which can form one or more 3- to 6-membered carbonaceous rings. The term "unsaturated hydrocarbonaceous chain" is understood to mean a chain which can comprise at least one double bond and/or at least one triple bond, it being possible for this hydrocarbonaceous chain to result in aromatic groups.

$X^-$ is chosen from organic and inorganic cosmetically acceptable anions, for example halides, such as chloride, bromide, fluoride or iodide; a hydroxide; a sulphate; a hydrogensulphate; a ($C_1$–$C_6$)alkyl sulphate, such as, for example, a methyl sulphate or an ethyl sulphate; an acetate; a tartrate; an oxalate; a ($C_1$–$C_6$)alkylsulphonate, such as methylsulphonate; and an arylsulphonate which is unsubstituted or substituted by at least one $C_1$–$C_4$ alkyl radical, such as, for example, a 4-toluylsulphonate.

According to one aspect of the disclosure, $W_3$ (formula I) can be chosen from a hydrogen atom and $C_1$–$C_4$ alkyl radicals optionally substituted with at least one radical chosen from hydroxyl, $C_1$–$C_2$ alkoxy, amino, and (di)($C_1$–$C_2$)alkylamino radicals.

According to one aspect of the disclosure, $W_3$ (formula I) can be chosen from a hydrogen atom and methyl, ethyl, and 2-hydroxyethyl radicals, for instance a hydrogen atom.

According to another aspect of the disclosure, $W_5$ (formula I) can be chosen from pyrazolyl, pyrrolyl, and imidazolyl rings, for example from pyrrolyl and imidazolyl rings.

According to one aspect, $W_5$ (formula I) can be a 5-membered nitrogenous heteroaromatic ring substituted with at least one $C_1$–$C_6$ alkyl radical optionally substituted by at least one entity chosen from hydroxyl, $C_1$–$C_4$ alkoxy, amino, and (di)($C_1$–$C_4$)alkylamino radicals; chlorine and fluorine atoms; ($C_1$–$C_4$)alkoxycarbonyl radicals; phenyl radicals optionally substituted by at least one entity chosen from hydroxyl, $C_1$–$C_2$ alkoxy, amino, $C_1$–$C_2$ monoalkylamino, and di($C_1$–$C_2$)alkylamino radicals, bromine and chlorine atoms; and di($C_1$–$C_2$)alkylamino and $C_1$–$C_2$ alkoxy radicals.

According to one aspect, $W_5$ (formula I) can be chosen from pyrrolyl and imidazolyl radicals, which are optionally substituted by at least one entity chosen from methyl, ethyl, propyl, phenyl, 4-chlorophenyl, and ethoxycarbonyl radicals.

Among the substituents $R_1$, $R_2$, $R_9$ and $R_{12}$, which may be identical or different, they may be chosen from $C_1$–$C_4$ alkyl radicals optionally substituted with at least one radical chosen from hydroxyl, $C_1$–$C_2$ alkoxy, amino, and (di)($C_1$–$C_2$)alkylamino radicals.

According to one aspect of the disclosure, $R_1$, $R_2$, $R_9$ and $R_{12}$, which may be identical or different, may be chosen from methyl, ethyl, propyl, and 2-hydroxyethyl radicals.

Among the substituents $R_5$, $R_6$, $R_7$ and $R_8$, which may be identical or different, they may be chosen from a hydrogen atom and methyl, ethyl, isopropyl, methoxymethyl, hydroxymethyl, 1-carboxymethyl, 1-aminomethyl, 2-carboxyethyl, 2-hydroxyethyl, 3-hydroxypropyl, 1,2-dihydroxyethyl, 1-hydroxy-2-aminoethyl, 2-hydroxy-1-aminoethyl, methoxy, ethoxy, 2-hydroxyethyloxy, and 2-aminoethyloxy radicals.

According to one aspect, $R_5$, $R_6$, $R_7$ and $R_8$, which may be identical or different, may be chosen from a hydrogen atom and methyl, hydroxymethyl, 2-hydroxyethyl, 1,2-dihydroxyethyl, methoxy, and 2-hydroxyethyloxy radicals, for example from a hydrogen atom, a methyl radical, and a methoxy radical.

Among the substituents, $R_3$, $R_4$, $R_{10}$, $R_{11}$, $R_{13}$, $R_{14}$ and $R_{15}$, which are identical or different, they may be chosen from a hydrogen atom; linear and branched $C_1$–$C_4$ alkyl radicals optionally substituted with at least one radical chosen from hydroxyl, $C_1$–$C_2$ alkoxy, $C_2$–$C_4$ (poly)hydroxyalkoxy, amino and (di)($C_1$–$C_2$)alkylamino radicals; a phenyl radical optionally substituted with at least one radical chosen from hydroxyl, $C_1$–$C_2$ alkoxy, $C_2$–$C_4$ (poly)hydroxyalkoxy, amino and (di)($C_1$–$C_2$)alkylamino radicals, and halogen atoms, such as chlorine, fluorine and bromine; sulphonylamino radicals; $C_1$–$C_2$ alkoxy radicals; $C_2$–$C_4$ (poly)hydroxyalkoxy radicals; amino radicals; (di)($C_1$–$C_2$) alkylamino radicals; and $C_2$–$C_4$ (poly)hydroxyalkylamino radicals.

According to an aspect of the disclosure, $R_3$, $R_4$, $R_{10}$, $R_{11}$, $R_{13}$, $R_{14}$ and $R_{15}$, which may be identical or different, they may be chosen from a hydrogen atom, $C_1$–$C_4$ alkyl radicals optionally substituted with at least one radical chosen from hydroxyl, amino and (di)($C_1$–$C_2$)alkylamino radicals; $C_1$–$C_2$ alkoxy radicals; amino radicals; (di)($C_1$–$C_2$) alkylamino radicals; and $C_2$–$C_4$ (poly)hydroxyalkylamino radicals.

According to an aspect of the disclosure, $R_3$, $R_4$, $R_{10}$, $R_{11}$, $R_{13}$, $R_{14}$ and $R_{15}$, which may be identical or different, are chosen from a hydrogen atom and methyl, phenyl, 2-hydroxymethyl, methoxy, ethoxy, 2-hydroxyethyloxy, amino, methylamino, dimethylamino, and 2-hydroxyethylamino radicals.

According to one aspect of the disclosure, in the formula (II), $Z_1$ is chosen from $NR_2$ radicals.

According to one aspect of the disclosure, in the formula (II), $Z_2$ is chosen from $CR_4$ radicals.

According to one aspect of the disclosure, in the formula (II), $Z_3$ is chosen from $CR_{13}$ radicals.

According to one aspect of the disclosure, in the formula (III), $Z_4$ is chosen from $CR_{14}$ radicals.

According to one aspect of the disclosure, in the formula (III), $Z_5$ is chosen from $CR_{15}$ radicals.

Mention may also be made, for example, among the monocationic monoazo dyes of formula (I):
2-(4-amino-N-(4-(N-pyrrolophenyl))phenylazo)-1,3-dimethyl-3H-imidazol-1-ium,
2-(4-amino-N-(4-(N-(2,5-dimethyl)pyrrolophenyl))phenylazo)-1,3-dimethyl-3H-imidazol-1-ium,
2-(4-amino-N-(4-(N-(2,5-diethyl)pyrrolophenyl))phenylazo)-1,3-dimethyl-3H-imidazol-1-ium,
2-(4-amino-N-(4-(N-(2,5-propyl)pyrrolophenyl))phenylazo)-1,3-dimethyl-3H-imidazol-1-ium,
2-(4-amino-N-(4-(N-(2-methyl-5-ethyl)pyrrolophenyl))phenylazo)-1,3-dimethyl-3H-imidazol-1-ium, 2-(4-amino-N-(4-(N-(2-methyl-5-propyl)pyrrolophenyl))
phenylazo)-1,3-dimethyl-3H-imidazol-1-ium,
2-(4-amino-N-(4-(N-(2-methyl-5-phenyl)pyrrolophenyl))
phenylazo)-1,3-dimethyl-3H-imidazol-1-ium,
2-(4-amino-N-(4-(N-[2-methyl-3-carboxyethyl-5-(4-chlorophenyl)pyrrolophenyl]phenylazo)-1,3-dimethyl-3H-imidazol-1-ium,
2-(4-amino-N-(4-(N-[2-5-(4-fluorophenyl)pyrrolophenyl]
phenylazo)-1,3-dimethyl-3H-imidazol-1-ium,
2-(4-amino-N-(4-(N-[2-methyl-5-(4-chlorophenyl)
pyrrolophenyl]phenylazo)-1,3-dimethyl-3H-imidazol-1-ium,
2-(4-amino-N-(4-(N-[2-(tert-butyl)-5-carboxyethyl
pyrrolophenyl]phenylazo)-1,3-dimethyl-3H-imidazol-1-ium,
2-(4-amino-N-(4-(N-[2-methyl-4-carboxyethyl-5-phenyl)
pyrrolophenyl]phenylazo)-1,3-dimethyl-3H-imidazol-1-ium,
2-(4-amino-N-(4-(N-[2-methyl-4-methyl-5-(4-methoxyphenyl))pyrrolophenyl]phenylazo)-1,3-dimethyl-3H-imidazol-1-ium,
2-(4-amino-N-(4-(N-[2,5-dimethyl-3,4-diisopropyl)
pyrrolophenyl]phenylazo)-1,3-dimethyl-3H-imidazol-1-ium,
2-(4-amino-N-(4-(N-pyrrolophenyl))phenylazo)-1,3-diethyl-3H-imidazol-1-ium,
2-(4-amino-N-(4-(N-(2,5-dimethyl)pyrrolophenyl))
phenylazo)-1,3-diethyl-3H-imidazol-1-ium,
2-(4-amino-N-(4-(N-(2,5-diethyl)pyrrolophenyl))
phenylazo)-1,3-diethyl-3H-imidazol-1-ium,
2-(4-amino-N-(4-(N-(2,5-propyl)pyrrolophenyl))
phenylazo)-1,3-diethyl-3H-imidazol-1-ium,
2-(4-amino-N-(4-(N-(2-methyl-5-ethyl)pyrrolophenyl))
phenylazo)-1,3-diethyl-3H-imidazol-1-ium,
2-(4-amino-N-(4-(N-(2-methyl-5-propyl)pyrrolophenyl))
phenylazo)-1,3-diethyl-3H-imidazol-1-ium,
2-(4-amino-N-(4-(N-(2-methyl-5-phenyl)pyrrolophenyl))
phenylazo)-1,3-diethyl-3H-imidazol-1-ium,
2-(4-amino-N-(4-(N-pyrrolophenyl))phenylazo)-1,3-dipropyl-3H-imidazol-1-ium,
2-(4-amino-N-(4-(N-(2,5-dimethyl)pyrrolophenyl))
phenylazo)-1,3-dipropyl-3H-imidazol-1-ium,
2-(4-amino-N-(4-(N-(2,5-diethyl)pyrrolophenyl))
phenylazo)-1,3-dipropyl-3H-imidazol-1-ium,
2-(4-amino-N-(4-(N-(2,5-propyl)pyrrolophenyl))
phenylazo)-1,3-dipropyl-3H-imidazol-1-ium,
2-(4-amino-N-(4-(N-(2-methyl-5-ethyl)pyrrolophenyl))
phenylazo)-1,3-dipropyl-3H-imidazol-1-ium,
2-(4-amino-N-(4-(N-(2-methyl-5-propyl)pyrrolophenyl))
phenylazo)-1,3-dipropyl-3H-imidazol-1-ium,
2-(4-amino-N-(4-(N-(2-methyl-5-phenyl)pyrrolophenyl))
phenylazo)-1,3-dipropyl-3H-imidazol-1-ium,
2-(4-amino-N-(4-(N-pyrrolophenyl))phenylazo)-1,3-di(2-hydroxyethyl)-3H-imidazol-1-ium,
2-(4-amino-N-(4-(N-(2,5-dimethyl)pyrrolophenyl))
phenylazo)-1,3-di(2-hydroxyethyl)-3H-imidazol-1-ium,
2-(4-amino-N-(4-(N-(2,5-diethyl)pyrrolophenyl))
phenylazo)-1,3-di(2-hydroxyethyl)-3H-imidazol-1-ium,
2-(4-amino-N-(4-(N-(2,5-propyl)pyrrolophenyl))
phenylazo)-1,3-di(2-hydroxyethyl)-3H-imidazol-1-ium,
2-(4-amino-N-(4-(N-(2-methyl-5-ethyl)pyrrolophenyl))
phenylazo)-1,3-di(2-hydroxyethyl)-3H-imidazol-1-ium,
2-(4-amino-N-(4-(N-(2-methyl-5-propyl)pyrrolophenyl))
phenylazo)-1,3-di(2-hydroxyethyl)-3H-imidazol-1-ium,
2-(4-amino-N-(4-(N-(2-methyl-5-phenyl)pyrrolophenyl))
phenylazo)-1,3-di(2-hydroxyethyl)-3H-imidazol-1-ium,
2-(4-amino-N-(4-(N-pyrrolophenyl))phenylazo)-4-phenyl-1,3-dimethyl-3H-imidazol-1-ium,
2-(4-amino-N-(4-(N-(2,5-dimethyl)pyrrolophenyl))
phenylazo)-4-phenyl-1,3-dimethyl-3H-imidazol-1-ium,
2-(4-amino-N-(4-(N-(2,5-diethyl)pyrrolophenyl))
phenylazo)-4-phenyl-1,3-dimethyl-3H-imidazol-1-ium,
2-(4-amino-N-(4-(N-(2,5-propyl)pyrrolophenyl))
phenylazo)-4-phenyl-1,3-dimethyl-3H-imidazol-1-ium,
2-(4-amino-N-(4-(N-(2-methyl-5-ethyl)pyrrolophenyl))
phenylazo)-4-phenyl-1,3-dimethyl-3H-imidazol-1-ium,
2-(4-amino-N-(4-(N-(2-methyl-5-propyl)pyrrolophenyl))
phenylazo)-4-phenyl-1,3-dimethyl-3H-imidazol-1-ium,
2-(4-amino-N-(4-(N-(2-methyl-5-phenyl)pyrrolophenyl))
phenylazo)-4-phenyl-1,3-dimethyl-3H-imidazol-1-ium,
2-(4-amino-N-(4-(N-[2-methyl-3-carboxyethyl-5-(4-chlorophenyl)pyrrolophenyl]phenylazo)-4-phenyl-1,3-dimethyl-3H-imidazol-1-ium,
2-(4-amino-N-(4-(N-[2-5-(4-fluorophenyl)pyrrolophenyl]
phenylazo)-4-phenyl-1,3-dimethyl-3H-imidazol-1-ium,
2-(4-amino-N-(4-(N-[2-methyl-5-(4-chlorophenyl)
pyrrolophenyl]phenylazo)-4-phenyl-1,3-dimethyl-3H-imidazol-1-ium,
2-(4-amino-N-(4-(N-[2-(tert-butyl)-5-carboxyethyl
pyrrolophenyl]phenylazo)-4-phenyl-1,3-dimethyl-3H-imidazol-1-ium,
2-(4-amino-N-(4-(N-[2-methyl-4-carboxyethyl-5-phenyl)
pyrrolophenyl]phenylazo)-4-phenyl-1,3-dimethyl-3H-imidazol-1-ium,
2-(4-amino-N-(4-(N-[2-methyl-4-methyl-5-(4-methoxyphenyl))pyrrolophenyl]phenylazo)-4-phenyl-1,3-dimethyl-3H-imidazol-1-ium,
2-(4-amino-N-(4-(N-[2,5-dimethyl-3,4-diisopropyl)
pyrrolophenyl]phenylazo)-4-phenyl-1,3-dimethyl-3H-imidazol-1-ium,
2-(4-amino-N-(4-(N-pyrrolophenyl))phenylazo)-4-phenyl-1,3-diethyl-3H-imidazol-1-ium,
2-(4-amino-N-(4-(N-(2,5-dimethyl)pyrrolophenyl))
phenylazo)-4-phenyl-1,3-diethyl-3H-imidazol-1-ium,
2-(4-amino-N-(4-(N-(2,5-diethyl)pyrrolophenyl))
phenylazo)-4-phenyl-1,3-diethyl-3H-imidazol-1-ium,
2-(4-amino-N-(4-(N-(2,5-propyl)pyrrolophenyl))
phenylazo)-4-phenyl-1,3-diethyl-3H-imidazol-1-ium,
2-(4-amino-N-(4-(N-(2-methyl-5-ethyl)pyrrolophenyl))
phenylazo)-4-phenyl-1,3-diethyl-3H-imidazol-1-ium,
2-(4-amino-N-(4-(N-(2-methyl-5-propyl)pyrrolophenyl))
phenylazo)-4-phenyl-1,3-diethyl-3H-imidazol-1-ium,
2-(4-amino-N-(4-(N-(2-methyl-5-phenyl)pyrrolophenyl))
phenylazo)-4-phenyl-1,3-diethyl-3H-imidazol-1-ium,
2-(4-amino-N-(4-(N-pyrrolophenyl))phenylazo)-4-phenyl-1,3-dipropyl-3H-imidazol-1-ium,
2-(4-amino-N-(4-(N-(2,5-dimethyl)pyrrolophenyl))
phenylazo)-4-phenyl-1,3-dipropyl-3H-imidazol-1-ium,
2-(4-amino-N-(4-(N-(2,5-diethyl)pyrrolophenyl))
phenylazo)-4-phenyl-1,3-dipropyl-3H-imidazol-1-ium,
2-(4-amino-N-(4-(N-(2,5-propyl)pyrrolophenyl))
phenylazo)-4-phenyl-1,3-dipropyl-3H-imidazol-1-ium,
2-(4-amino-N-(4-(N-(2-methyl-5-ethyl)pyrrolophenyl))
phenylazo)-4-phenyl-1,3-dipropyl-3H-imidazol-1-ium,
2-(4-amino-N-(4-(N-(2-methyl-5-propyl)pyrrolophenyl))
phenylazo)-4-phenyl-1,3-dipropyl-3H-imidazol-1-ium,
2-(4-amino-N-(4-(N-(2-methyl-5-phenyl)pyrrolophenyl))
phenylazo)-4-phenyl-1,3-dipropyl-3H-imidazol-1-ium,
2-(4-amino-N-(4-(N-pyrrolophenyl))phenylazo)-4-phenyl-1,3-di(2-hydroxyethyl)-3H-imidazol-1-ium,
2-(4-amino-N-(4-(N-(2,5-dimethyl)pyrrolophenyl))
phenylazo)-4-phenyl-1,3-di(2-hydroxyethyl)-3H-imidazol-1-ium,
2-(4-amino-N-(4-(N-(2,5-diethyl)pyrrolophenyl))
phenylazo)-4-phenyl-1,3-di(2-hydroxyethyl)-3H-imidazol-1-ium, 2-(4-amino-N-(4-(N-(2,5-propyl)pyrrolophenyl))
phenylazo)-4-phenyl-1,3-di(2-hydroxyethyl)-3H-
imidazol-1-ium,
2-(4-amino-N-(4-(N-(2-methyl-5-ethyl)pyrrolophenyl))
phenylazo)-4-phenyl-1,3-di(2-hydroxyethyl)-3H-
imidazol-1-ium,
2-(4-amino-N-(4-(N-(2-methyl-5-propyl)pyrrolophenyl))
phenylazo)-4-phenyl-1,3-di(2-hydroxyethyl)-3H-
imidazol-1-ium,
2-(4-amino-N-(4-(N-(2-methyl-5-phenyl)pyrrolophenyl))
phenylazo)-4-phenyl-1,3-di(2-hydroxyethyl)-3H-
imidazol-1-ium,
2-(4-amino-N-(4-(N-pyrrolophenyl))phenylazo)-4-methyl-
1,3-dimethyl-3H-imidazol-1-ium,
2-(4-amino-N-(4-(N-(2,5-dimethyl)pyrrolophenyl))
phenylazo)-4-methyl-1,3-dimethyl-3H-imidazol-1-ium,
2-(4-amino-N-(4-(N-(2,5-diethyl)pyrrolophenyl))
phenylazo)-4-methyl-1,3-dimethyl-3H-imidazol-1-ium,
2-(4-amino-N-(4-(N-(2,5-propyl)pyrrolophenyl))
phenylazo)-4-methyl-1,3-dimethyl-3H-imidazol-1-ium,
2-(4-amino-N-(4-(N-(2-methyl-5-ethyl)pyrrolophenyl))
phenylazo)-4-methyl-1,3-dimethyl-3H-imidazol-1-ium,
2-(4-amino- N-(4-(N-(2-methyl-5-propyl)pyrrolophenyl))
phenylazo)-4-methyl-1,3-dimethyl-3H-imidazol-1-ium,
2-(4-amino-N-(4-(N-(2-methyl-5-phenyl)pyrrolophenyl))
phenylazo)-4-methyl-1,3-dimethyl-3H-imidazol-1-ium,
2-(4-amino-N-(4-(N-[2-methyl-3-carboxyethyl-5-(4-
chlorophenyl)pyrrolophenyl]phenylazo)-4-methyl-1,3-
dimethyl-3H-imidazol-1-ium,
2-(4-amino-N-(4-(N-[2-5-(4-fluorophenyl)pyrrolophenyl]
phenylazo)-4-methyl-1,3-dimethyl-3H-imidazol-1-ium,
2-(4-amino-N-(4-(N-[2-methyl-5-(4-chlorophenyl)
pyrrolophenyl]phenylazo)-4-methyl-1,3-dimethyl-3H-
imidazol-1-ium,
2-(4-amino-N-(4-(N-[2-(tert-butyl)-5-carboxyethyl)
pyrrolophenyl]phenylazo)-4-methyl-1,3-dimethyl-3H-
imidazol-1-ium,
2-(4-amino-N-(4-(N-[2-methyl-4-carboxyethyl-5-phenyl)
pyrrolophenyl]phenylazo)-4-methyl-1,3-dimethyl-3H-
imidazol-1-ium,
2-(4-amino-N-(4-(N-[2-methyl-4-methyl-5-(4-
methoxyphenyl))pyrrolophenyl]phenylazo)-4-methyl-1,
3-dimethyl-3H-imidazol-1-ium,
2-(4-amino-N-(4-(N-[2,5-dimethyl-3,4-diisopropyl)
pyrrolophenyl]phenylazo)-4-methyl-1,3-dimethyl-3H-
imidazol-1-ium,
2-(4-amino-N-(4-(N-pyrrolophenyl))phenylazo)-4-methyl-
1,3-diethyl-3H-imidazol-1-ium,
2-(4-amino-N-(4-(N-(2,5-dimethyl)pyrrolophenyl))
phenylazo)-4-methyl-1,3-diethyl-3H-imidazol-1-ium,
2-(4-amino-N-(4-(N-(2,5-diethyl)pyrrolophenyl))
phenylazo)-4-methyl-1,3-diethyl-3H-imidazol-1-ium,
2-(4-amino-N-(4-(N-(2,5-propyl)pyrrolophenyl))
phenylazo)-4-methyl-1,3-diethyl-3H-imidazol-1-ium,
2-(4-amino-N-(4-(N-(2-methyl-5-ethyl)pyrrolophenyl))
phenylazo)-4-methyl-1,3-diethyl-3H-imidazol-1-ium,
2-(4-amino-N-(4-(N-(2-methyl-5-propyl)pyrrolophenyl))
phenylazo)-4-methyl-1,3-diethyl-3H-imidazol-1-ium,
2-(4-amino-N-(4-(N-(2-methyl-5-phenyl)pyrrolophenyl))
phenylazo)-4-methyl-1,3-diethyl-3H-imidazol-1-ium,
2-(4-amino-N-(4-(N-pyrrolophenyl))phenylazo)-4-methyl-
1,3-dipropyl-3H-imidazol-1-ium,
2-(4-amino-N-(4-(N-(2,5-dimethyl)pyrrolophenyl))
phenylazo)-4-methyl-1,3-dipropyl-3H-imidazol-1-ium,
2-(4-amino-N-(4-(N-(2,5-diethyl)pyrrolophenyl))
phenylazo)-4-methyl-1,3-dipropyl-3H-imidazol-1-ium,
2-(4-amino-N-(4-(N-(2,5-propyl)pyrrolophenyl))
phenylazo)-4-methyl-1,3-dipropyl-3H-imidazol-1-ium,
2-(4-amino-N-(4-(N-(2-methyl-5-ethyl)pyrrolophenyl))
phenylazo)-4-methyl-1,3-dipropyl-3H-imidazol-1-ium,
2-(4-amino-N-(4-(N-(2-methyl-5-propyl)pyrrolophenyl))
phenylazo)-4-methyl-1,3-dipropyl-3H-imidazol-1-ium,
2-(4-amino-N-(4-(N-(2-methyl-5-phenyl)pyrrolophenyl))
phenylazo)-4-methyl-1,3-dipropyl-3H-imidazol-1-ium,
2-(4-amino-N-(4-(N-pyrrolophenyl))phenylazo)-4-methyl-
1,3-di(2-hydroxyethyl)-3H-imidazol-1-ium,
2-(4-amino-N-(4-(N-(2,5-dimethyl)pyrrolophenyl))
phenylazo)-4-methyl-1,3-di(2-hydroxyethyl)-3H-
imidazol-1-ium,
2-(4-amino-N-(4-(N-(2,5-diethyl)pyrrolophenyl))
phenylazo)-4-methyl-1,3-di(2-hydroxyethyl)-3H-
imidazol-1-ium,
2-(4-amino-N-(4-(N-(2,5-propyl)pyrrolophenyl))
phenylazo)-4-methyl-1,3-di(2-hydroxyethyl)-3H-
imidazol-1-ium,
2-(4-amino-N-(4-(N-(2-methyl-5-ethyl)pyrrolophenyl))
phenylazo)-4-methyl-1,3-di(2-hydroxyethyl)-3H-
imidazol-1-ium,
2-(4-amino-N-(4-(N-(2-methyl-5-propyl)pyrrolophenyl))
phenylazo)-4-methyl-1,3-di(2-hydroxyethyl)-3H-
imidazol-1-ium,
2-(4-amino-N-(4-(N-(2-methyl-5-phenyl)pyrrolophenyl))
phenylazo)-4-methyl-1,3-di(2-hydroxyethyl)-3H-
imidazol-1-ium,
2-(4-amino-N-(4-(N-pyrrolophenyl))phenylazo)-4-
hydroxymethyl-1,3-dimethyl-3H-imidazol-1-ium,
2-(4-amino-N-(4-(N-(2,5-dimethyl)pyrrolophenyl))
phenylazo)-4-hydroxymethyl-1,3-dimethyl-3H-imidazol-
1-ium,
2-(4-amino-N-(4-(N-(2,5-diethyl)pyrrolophenyl))
phenylazo)-4-hydroxymethyl-1,3-dimethyl-3H-imidazol-
1-ium,
2-(4-amino-N-(4-(N-(2,5-propyl)pyrrolophenyl))
phenylazo)-4-hydroxymethyl-1,3-dimethyl-3H-imidazol-
1-ium,
2-(4-amino-N-(4-(N-(2-methyl-5-ethyl)pyrrolophenyl))
phenylazo)-4-hydroxymethyl-1,3-dimethyl-3H-imidazol-
1-ium,
2-(4-amino-N-(4-(N-(2-methyl-5-propyl)pyrrolophenyl))
phenylazo)-4-hydroxymethyl-1,3-dimethyl-3H-imidazol-
1-ium,
2-(4-amino-N-(4-(N-(2-methyl-5-phenyl)pyrrolophenyl))
phenylazo)-4-hydroxymethyl-1,3-dimethyl-3H-imidazol-
1-ium,
2-(4-amino-N-(4-(N-[2-methyl-3-carboxyethyl-5-(4-
chlorophenyl)pyrrolophenyl]phenylazo)-4-
hydroxymethyl-1,3-dimethyl-3H-imidazol-1-ium,
2-(4-amino-N-(4-(N-[2-5-(4-fluorophenyl)pyrrolophenyl]
phenylazo)-4-hydroxymethyl-1,3-dimethyl-3H-imidazol-
1-ium,
2-(4-amino-N-(4-(N-[2-methyl-5-(4-chlorophenyl)
pyrrolophenyl]phenylazo)-4-hydroxymethyl-1,3-
dimethyl-3H-imidazol-1-ium,
2-(4-amino-N-(4-(N-[2-(tert-butyl)-5-carboxyethyl)
pyrrolophenyl]phenylazo)-4-hydroxymethyl-1,3-
dimethyl-3H-imidazol-1-ium,
2-(4-amino-N-(4-(N-[2-methyl-4-carboxyethyl-5-phenyl)
pyrrolophenyl]phenylazo)-4-hydroxymethyl-1,3-
dimethyl-3H-imidazol-1-ium,
2-(4-amino-N-(4-(N-[2-methyl-4-methyl-5-(4-
methoxyphenyl))pyrrolophenyl]phenylazo)-4-
hydroxymethyl-1,3-dimethyl-3H-imidazol-1-ium,
2-(4-amino-N-(4-(N-[2,5-dimethyl-3,4-diisopropyl)
pyrrolophenyl]phenylazo)-4-hydroxymethyl-1,3-
dimethyl-3H-imidazol-1-ium, 2-(4-amino-N-(4-(N-pyrrolophenyl))phenylazo)-4-hydroxymethyl-1,3-diethyl-3H-imidazol-1-ium,
2-(4-amino-N-(4-(N-(2,5-dimethyl)pyrrolophenyl))phenylazo)-4-hydroxymethyl-1,3-diethyl-3H-imidazol-1-ium,
2-(4-amino-N-(4-(N-(2,5-diethyl)pyrrolophenyl))phenylazo)-4-hydroxymethyl-1,3-diethyl-3H-imidazol-1-ium,
2-(4-amino-N-(4-(N-(2,5-propyl)pyrrolophenyl))phenylazo)-4-hydroxymethyl-1,3-diethyl-3H-imidazol-1-ium,
2-(4-amino-N-(4-(N-(2-methyl-5-ethyl)pyrrolophenyl))phenylazo)-4-hydroxymethyl-1,3-diethyl-3H-imidazol-1-ium,
2-(4-amino-N-(4-(N-(2-methyl-5-propyl)pyrrolophenyl))phenylazo)-4-hydroxymethyl-1,3-diethyl-3H-imidazol-1-ium,
2-(4-amino-N-(4-(N-(2-methyl-5-phenyl)pyrrolophenyl))phenylazo)-4-hydroxymethyl-1,3-diethyl-3H-imidazol-1-ium,
2-(4-amino-N-(4-(N-pyrrolophenyl))phenylazo)-4-hydroxymethyl-1,3-dipropyl-3H-imidazol-1-ium,
2-(4-amino-N-(4-(N-(2,5-dimethyl)pyrrolophenyl))phenylazo)-4-hydroxymethyl-1,3-dipropyl-3H-imidazol-1-ium,
2-(4-amino-N-(4-(N-(2,5-diethyl)pyrrolophenyl))phenylazo)-4-hydroxymethyl-1,3-dipropyl-3H-imidazol-1-ium,
2-(4-amino-N-(4-(N-(2,5-propyl)pyrrolophenyl))phenylazo)-4-hydroxymethyl-1,3-dipropyl-3H-imidazol-1-ium,
2-(4-amino-N-(4-(N-(2-methyl-5-ethyl)pyrrolophenyl))phenylazo)-4-hydroxymethyl-1,3-dipropyl-3H-imidazol-1-ium,
2-(4-amino-N-(4-(N-(2-methyl-5-propyl)pyrrolophenyl))phenylazo)-4-hydroxymethyl-1,3-dipropyl-3H-imidazol-1-ium,
2-(4-amino-N-(4-(N-(2-methyl-5-phenyl)pyrrolophenyl))phenylazo)-4-hydroxymethyl-1,3-dipropyl-3H-imidazol-1-ium,
2-(4-amino-N-(4-(N-pyrrolophenyl))phenylazo)-4-hydroxymethyl-1,3-di(2-hydroxyethyl)-3H-imidazol-1-ium,
2-(4-amino-N-(4-(N-(2,5-dimethyl)pyrrolophenyl))phenylazo)-4-hydroxymethyl-1,3-di(2-hydroxyethyl)-3H-imidazol-1-ium,
2-(4-amino-N-(4-(N-(2,5-diethyl)pyrrolophenyl))phenylazo)-4-hydroxymethyl-1,3-di(2-hydroxyethyl)-3H-imidazol-1-ium,
2-(4-amino-N-(4-(N-(2,5-propyl)pyrrolophenyl))phenylazo)-4-hydroxymethyl-1,3-di(2-hydroxyethyl)-3H-imidazol-1-ium,
2-(4-amino-N-(4-(N-(2-methyl-5-ethyl)pyrrolophenyl))phenylazo)-4-hydroxymethyl-1,3-di(2-hydroxyethyl)-3H-imidazol-1-ium,
2-(4-amino-N-(4-(N-(2-methyl-5-propyl)pyrrolophenyl))phenylazo)-4-hydroxymethyl-1,3-di(2-hydroxyethyl)-3H-imidazol-1-ium,
2-(4-amino-N-(4-(N-(2-methyl-5-phenyl)pyrrolophenyl))phenylazo)-4-hydroxymethyl-1,3-di(2-hydroxyethyl)-3H-imidazol-1-ium,
2-(4-amino-N-(4-(N-imidazolophenyl))phenylazo)-1,3-dimethyl-3H-imidazol-1-ium,
2-(4-amino-N-(4-(N-imidazolophenyl))phenylazo)-1,3-diethyl-3H-imidazol-1-ium,
2-(4-amino-N-(4-(N-imidazolophenyl))phenylazo)-1,3-dipropyl-3H-imidazol-1-ium,
2-(4-amino-N-(4-(N-imidazolophenyl))phenylazo)-1,3-di(2-hydroxyethyl)-3H-imidazol-1-ium,
2-(4-amino-N-(4-(N-pyrrolophenyl))phenylazo)-1-methylpyridin-1-ium,
2-(4-amino-N-(4-(N-(2,5-dimethyl)pyrrolophenyl))phenylazo)-1-methylpyridin-1-ium,
2-(4-amino-N-(4-(N-(2,5-diethyl)pyrrolophenyl))phenylazo)-1-methylpyridin-1-ium,
2-(4-amino-N-(4-(N-(2,5-propyl)pyrrolophenyl))phenylazo)-1-methylpyridin-1-ium,
2-(4-amino-N-(4-(N-(2-methyl-5-ethyl)pyrrolophenyl))phenylazo)-1-methylpyridin-1-ium,
2-(4-amino-N-(4-(N-(2-methyl-5-propyl)pyrrolophenyl))phenylazo)-1-methylpyridin-1-ium,
2-(4-amino-N-(4-(N-(2-methyl-5-phenyl)pyrrolophenyl))phenylazo)-1-methylpyridin-1-ium,
2-(4-amino-N-(4-(N-pyrrolophenyl))phenylazo)-1-ethylpyridin-1-ium,
2-(4-amino-N-(4-(N-(2,5-dimethyl)pyrrolophenyl))phenylazo)-1-ethylpyridin-1-ium,
2-(4-amino-N-(4-(N-(2,5-diethyl)pyrrolophenyl))phenylazo)-1-ethylpyridin-1-ium,
2-(4-amino-N-(4-(N-(2,5-propyl)pyrrolophenyl))phenylazo)-1-ethylpyridin-1-ium,
2-(4-amino-N-(4-(N-(2-methyl-5-ethyl)pyrrolophenyl))phenylazo)-1-ethylpyridin-1-ium,
2-(4-amino-N-(4-(N-(2-methyl-5-propyl)pyrrolophenyl))phenylazo)-1-ethylpyridin-1-ium,
2-(4-amino-N-(4-(N-(2-methyl-5-phenyl)pyrrolophenyl))phenylazo)-1-ethylpyridin-1-ium,
2-(4-amino-N-(4-(N-pyrrolophenyl))phenylazo)-1-propylpyridin-1-ium,
2-(4-amino-N-(4-(N-(2,5-dimethyl)pyrrolophenyl))phenylazo)-1-propylpyridin-1-ium,
2-(4-amino-N-(4-(N-(2,5-diethyl)pyrrolophenyl))phenylazo)-1-propylpyridin-1-ium,
2-(4-amino-N-(4-(N-(2,5-propyl)pyrrolophenyl))phenylazo)-1-propylpyridin-1-ium,
2-(4-amino-N-(4-(N-(2-methyl-5-ethyl)pyrrolophenyl))phenylazo)-1-propylpyridin-1-ium,
2-(4-amino-N-(4-(N-(2-methyl-5-propyl)pyrrolophenyl))phenylazo)-1-propylpyridin-1-ium,
2-(4-amino-N-(4-(N-(2-methyl-5-phenyl)pyrrolophenyl))phenylazo)-1-propylpyridin-1-ium,
2-(4-amino-N-(4-(N-pyrrolophenyl))phenylazo)-1-(2-hydroxyethyl)pyridin-1-ium,
2-(4-amino-N-(4-(N-(2,5-dimethyl)pyrrolophenyl))phenylazo)-1-(2-hydroxyethyl)pyridin-1-ium,
2-(4-amino-N-(4-(N-(2,5-diethyl)pyrrolophenyl))phenylazo)-1-(2-hydroxyethyl)pyridin-1-ium,
2-(4-amino-N-(4-(N-(2,5-propyl)pyrrolophenyl))phenylazo)-1-(2-hydroxyethyl)pyridin-1-ium,
2-(4-amino-N-(4-(N-(2-methyl-5-ethyl)pyrrolophenyl))phenylazo)-1-(2-hydroxyethyl)pyridin-1-ium,
2-(4-amino-N-(4-(N-(2-methyl-5-propyl)pyrrolophenyl))phenylazo)-1-(2-hydroxyethyl)pyridin-1-ium,
2-(4-amino-N-(4-(N-(2-methyl-5-phenyl)pyrrolophenyl))phenylazo)-1-(2-hydroxyethyl)pyridin-1-ium,
2-(4-amino-N-(4-(N-pyrrolophenyl))phenylazo)-1,3-dimethylpyridin-1-ium,
2-(4-amino-N-(4-(N-(2,5-dimethyl)pyrrolophenyl))phenylazo)-1,3-dimethylpyridin-1-ium,
2-(4-amino-N-(4-(N-(2,5-diethyl)pyrrolophenyl))phenylazo)-1,3-dimethylpyridin-1-ium,
2-(4-amino-N-(4-(N-(2,5-propyl)pyrrolophenyl))phenylazo)-1,3-dimethylpyridin-1-ium,
2-(4-amino-N-(4-(N-(2-methyl-5-ethyl)pyrrolophenyl))phenylazo)-1,3-dimethylpyridin-1-ium, 2-(4-amino-N-(4-(N-(2-methyl-5-propyl)pyrrolophenyl)) phenylazo)-1,3-dimethylpyridin-1-ium,
2-(4-amino-N-(4-(N-(2-methyl-5-phenyl)pyrrolophenyl)) phenylazo)-1,3-dimethylpyridin-1-ium,
2-(4-amino-N-(4-(N-pyrrolophenyl))phenylazo)-1-ethyl-3-methylpyridin-1-ium,
2-(4-amino-N-(4-(N-(2,5-dimethyl)pyrrolophenyl)) phenylazo)-1-ethyl-3-methylpyridin-1-ium,
2-(4-amino-N-(4-(N-(2,5-diethyl)pyrrolophenyl)) phenylazo)-1-ethyl-3-methylpyridin-1-ium,
2-(4-amino-N-(4-(N-(2,5-propyl)pyrrolophenyl)) phenylazo)-1-ethyl-3-methylpyridin-1-ium,
2-(4-amino-N-(4-(N-(2-methyl-5-ethyl)pyrrolophenyl)) phenylazo)-1-ethyl-3-methylpyridin-1-ium,
2-(4-amino-N-(4-(N-(2-methyl-5-propyl)pyrrolophenyl)) phenylazo)-1-ethyl-3-methylpyridin-1-ium,
2-(4-amino-N-(4-(N-(2-methyl-5-phenyl)pyrrolophenyl)) phenylazo)-1-ethyl-3-methylpyridin-1-ium,
2-(4-amino-N-(4-(N-pyrrolophenyl))phenylazo)-1-propyl-3-methylpyridin-1-ium,
2-(4-amino-N-(4-(N-(2,5-dimethyl)pyrrolophenyl)) phenylazo)-1-propyl-3-methylpyridin-1-ium,
2-(4-amino-N-(4-(N-(2,5-diethyl)pyrrolophenyl)) phenylazo)-1-propyl-3-methylpyridin-1-ium,
2-(4-amino-N-(4-(N-(2,5-propyl)pyrrolophenyl)) phenylazo)-1-propyl-3-methylpyridin-1-ium,
2-(4-amino-N-(4-(N-(2-methyl-5-ethyl)pyrrolophenyl)) phenylazo)-1-propyl-3-methylpyridin-1-ium,
2-(4-amino-N-(4-(N-(2-methyl-5-propyl)pyrrolophenyl)) phenylazo)-1-propyl-3-methylpyridin-1-ium,
2-(4-amino-N-(4-(N-(2-methyl-5-phenyl)pyrrolophenyl)) phenylazo)-1-propyl-3-methylpyridin-1-ium,
2-(4-amino-N-(4-(N-pyrrolophenyl))phenylazo)-1-(2-hydroxyethyl)-3-methylpyridin-1-ium,
2-(4-amino-N-(4-(N-(2,5-dimethyl)pyrrolophenyl)) phenylazo)-1-(2-hydroxyethyl)-3-methylpyridin-1-ium,
2-(4-amino-N-(4-(N-(2,5-diethyl)pyrrolophenyl)) phenylazo)-1-(2-hydroxyethyl)-3-methylpyridin-1-ium,
2-(4-amino-N-(4-(N-(2,5-propyl)pyrrolophenyl)) phenylazo)-1-(2-hydroxyethyl)-3-methylpyridin-1-ium,
2-(4-amino-N-(4-(N-(2-methyl-5-ethyl)pyrrolophenyl)) phenylazo)-1-(2-hydroxyethyl)-3-methylpyridin-1-ium,
2-(4-amino-N-(4-(N-(2-methyl-5-propyl)pyrrolophenyl)) phenylazo)-1-(2-hydroxyethyl)-3-methylpyridin-1-ium,
2-(4-amino-N-(4-(N-(2-methyl-5-phenyl)pyrrolophenyl)) phenylazo)-1-(2-hydroxyethyl)-3-methylpyridin-1-ium,
2-(4-amino-N-(4-(N-pyrrolophenyl))phenylazo)-1,4-dimethylpyridin-1-ium,
2-(4-amino-N-(4-(N-(2,5-dimethyl)pyrrolophenyl)) phenylazo)-1,4-dimethylpyridin-1-ium,
2-(4-amino-N-(4-(N-(2,5-diethyl)pyrrolophenyl)) phenylazo)-1,4-dimethylpyridin-1-ium,
2-(4-amino-N-(4-(N-(2,5-propyl)pyrrolophenyl)) phenylazo)-1,4-dimethylpyridin-1-ium,
2-(4-amino-N-(4-(N-(2-methyl-5-ethyl)pyrrolophenyl)) phenylazo)-1,4-dimethylpyridin-1-ium,
2-(4-amino-N-(4-(N-(2-methyl-5-propyl)pyrrolophenyl)) phenylazo)-1,4-dimethylpyridin-1-ium,
2-(4-amino-N-(4-(N-(2-methyl-5-phenyl)pyrrolophenyl)) phenylazo)-1,4-dimethylpyridin-1-ium,
2-(4-amino-N-(4-(N-pyrrolophenyl))phenylazo)-1-ethyl-4-methylpyridin-1-ium,
2-(4-amino-N-(4-(N-(2,5-dimethyl)pyrrolophenyl)) phenylazo)-1-ethyl-4-methylpyridin-1-ium,
2-(4-amino-N-(4-(N-(2,5-diethyl)pyrrolophenyl)) phenylazo)-1-ethyl-4-methylpyridin-1-ium,
2-(4-amino-N-(4-(N-(2,5-propyl)pyrrolophenyl)) phenylazo)-1-ethyl-4-methylpyridin-1-ium,
2-(4-amino-N-(4-(N-(2-methyl-5-ethyl)pyrrolophenyl)) phenylazo)-1-ethyl-4-methylpyridin-1-ium,
2-(4-amino-N-(4-(N-(2-methyl-5-propyl)pyrrolophenyl)) phenylazo)-1-ethyl-4-methylpyridin-1-ium,
2-(4-amino-N-(4-(N-(2-methyl-5-phenyl)pyrrolophenyl)) phenylazo)-1-ethyl-4-methylpyridin-1-ium,
2-(4-amino-N-(4-(N-pyrrolophenyl))phenylazo)-1-propyl-4-methylpyridin-1-ium,
2-(4-amino-N-(4-(N-(2,5-dimethyl)pyrrolophenyl)) phenylazo)-1-propyl-4-methylpyridin-1-ium,
2-(4-amino-N-(4-(N-(2,5-diethyl)pyrrolophenyl)) phenylazo)-1-propyl-4-methylpyridin-1-ium,
2-(4-amino-N-(4-(N-(2,5-propyl)pyrrolophenyl)) phenylazo)-1-propyl-4-methylpyridin-1-ium,
2-(4-amino-N-(4-(N-(2-methyl-5-ethyl)pyrrolophenyl)) phenylazo)-1-propyl-4-methylpyridin-1-ium,
2-(4-amino-N-(4-(N-(2-methyl-5-propyl)pyrrolophenyl)) phenylazo)-1-propyl-4-methylpyridin-1-ium,
2-(4-amino-N-(4-(N-(2-methyl-5-phenyl)pyrrolophenyl)) phenylazo)-1-propyl-4-methylpyridin-1-ium,
2-(4-amino-N-(4-(N-pyrrolophenyl))phenylazo)-1-(2-hydroxyethyl)-4-methylpyridin-1-ium,
2-(4-amino-N-(4-(N-(2,5-dimethyl)pyrrolophenyl)) phenylazo)-1-(2-hydroxyethyl)-4-methylpyridin-1-ium,
2-(4-amino-N-(4-(N-(2,5-diethyl)pyrrolophenyl)) phenylazo)-1-(2-hydroxyethyl)-4-methylpyridin-1-ium,
2-(4-amino-N-(4-(N-(2,5-propyl)pyrrolophenyl)) phenylazo)-1-(2-hydroxyethyl)-4-methylpyridin-1-ium,
2-(4-amino-N-(4-(N-(2-methyl-5-ethyl)pyrrolophenyl)) phenylazo)-1-(2-hydroxyethyl)-4-methylpyridin-1-ium,
2-(4-amino-N-(4-(N-(2-methyl-5-propyl)pyrrolophenyl)) phenylazo)-1-(2-hydroxyethyl)-4-methylpyridin-1-ium,
2-(4-amino-N-(4-(N-(2-methyl-5-phenyl)pyrrolophenyl)) phenylazo)-1-(2-hydroxyethyl)-4-methylpyridin-1-ium,
2-(4-amino-N-(4-(N-pyrrolophenyl))phenylazo)-1,5-dimethylpyridin-1-ium,
2-(4-amino-N-(4-(N-(2,5-dimethyl)pyrrolophenyl)) phenylazo)-1,5-dimethylpyridin-1-ium,
2-(4-amino-N-(4-(N-(2,5-diethyl)pyrrolophenyl)) phenylazo)-1,5-dimethylpyridin-1-ium,
2-(4-amino-N-(4-(N-(2,5-propyl)pyrrolophenyl)) phenylazo)-1,5-dimethylpyridin-1-ium,
2-(4-amino-N-(4-(N-(2-methyl-5-ethyl)pyrrolophenyl)) phenylazo)-1,5-dimethylpyridin-1-ium,
2-(4-amino-N-(4-(N-(2-methyl-5-propyl)pyrrolophenyl)) phenylazo)-1,5-dimethylpyridin-1-ium,
2-(4-amino-N-(4-(N-(2-methyl-5-phenyl)pyrrolophenyl)) phenylazo)-1,5-dimethylpyridin-1-ium,
2-(4-amino-N-(4-(N-pyrrolophenyl))phenylazo)-1-ethyl-5-methylpyridin-1-ium,
2-(4-amino-N-(4-(N-(2,5-dimethyl)pyrrolophenyl)) phenylazo)-1-ethyl-5-methylpyridin-1-ium,
2-(4-amino-N-(4-(N-(2,5-diethyl)pyrrolophenyl)) phenylazo)-1-ethyl-5-methylpyridin-1-ium,
2-(4-amino-N-(4-(N-(2,5-propyl)pyrrolophenyl)) phenylazo)-1-ethyl-5-methylpyridin-1-ium,
2-(4-amino-N-(4-(N-(2-methyl-5-ethyl)pyrrolophenyl)) phenylazo)-1-ethyl-5-methylpyridin-1-ium,
2-(4-amino-N-(4-(N-(2-methyl-5-propyl)pyrrolophenyl)) phenylazo)-1-ethyl-5-methylpyridin-1-ium,
2-(4-amino-N-(4-(N-(2-methyl-5-phenyl)pyrrolophenyl)) phenylazo)-1-ethyl-5-methylpyridin-1-ium,
2-(4-amino-N-(4-(N-pyrrolophenyl))phenylazo)-1-propyl-5-methylpyridin-1-ium,
2-(4-amino-N-(4-(N-(2,5-dimethyl)pyrrolophenyl)) phenylazo)-1-propyl-5-methylpyridin-1-ium,
2-(4-amino-N-(4-(N-(2,5-diethyl)pyrrolophenyl)) phenylazo)-1-propyl-5-methylpyridin-1-ium, 2-(4-amino-N-(4-(N-(2,5-propyl)pyrrolophenyl))
phenylazo)-1-propyl-5-methylpyridin-1-ium,
2-(4-amino-N-(4-(N-(2-methyl-5-ethyl)pyrrolophenyl))
phenylazo)-1-propyl-5-methylpyridin-1-ium,
2-(4-amino-N-(4-(N-(2-methyl-5-propyl)pyrrolophenyl))
phenylazo)-1-propyl-5-methylpyridin-1-ium,
2-(4-amino-N-(4-(N-(2-methyl-5-phenyl)pyrrolophenyl))
phenylazo)-1-propyl-5-methylpyridin-1-ium,
2-(4-amino-N-(4-(N-pyrrolophenyl))phenylazo)-1-(2-hydroxyethyl)-5-methylpyridin-1-ium,
2-(4-amino-N-(4-(N-(2,5-dimethyl)pyrrolophenyl))
phenylazo)-1-(2-hydroxyethyl)-5-methylpyridin-1-ium,
2-(4-amino-N-(4-(N-(2,5-diethyl)pyrrolophenyl))
phenylazo)-1-(2-hydroxyethyl)-5-methylpyridin-1-ium,
2-(4-amino-N-(4-(N-(2,5-propyl)pyrrolophenyl))
phenylazo)-1-(2-hydroxyethyl)-5-methylpyridin-1-ium,
2-(4-amino-N-(4-(N-(2-methyl-5-ethyl)pyrrolophenyl))
phenylazo)-1-(2-hydroxyethyl)-5-methylpyridin-1-ium,
2-(4-amino-N-(4-(N-(2-methyl-5-propyl)pyrrolophenyl))
phenylazo)-1-(2-hydroxyethyl)-5-methylpyridin-1-ium,
2-(4-amino-N-(4-(N-(2-methyl-5-phenyl)pyrrolophenyl))
phenylazo)-1-(2-hydroxyethyl)-5-methylpyridin-1-ium,
2-(4-amino-N-(4-(N-pyrrolophenyl))phenylazo)-1,6-dimethylpyridin-1-ium,
2-(4-amino-N-(4-(N-(2,5-dimethyl)pyrrolophenyl))
phenylazo)-1,6-dimethylpyridin-1-ium,
2-(4-amino-N-(4-(N-(2,5-diethyl)pyrrolophenyl))
phenylazo)-1,6-dimethylpyridin-1-ium,
2-(4-amino-N-(4-(N-(2,5-propyl)pyrrolophenyl))
phenylazo)-1,6-dimethylpyridin-1-ium,
2-(4-amino-N-(4-(N-(2-methyl-5-ethyl)pyrrolophenyl))
phenylazo)-1,6-dimethylpyridin-1-ium,
2-(4-amino-N-(4-(N-(2-methyl-5-propyl)pyrrolophenyl))
phenylazo)-1,6-dimethylpyridin-1-ium,
2-(4-amino-N-(4-(N-(2-methyl-5-phenyl)pyrrolophenyl))
phenylazo)-1,6-dimethylpyridin-1-ium,
2-(4-amino-N-(4-(N-pyrrolophenyl))phenylazo)-1-ethyl-6-methylpyridin-1-ium,
2-(4-amino-N-(4-(N-(2,5-dimethyl)pyrrolophenyl))
phenylazo)-1-ethyl-6-methylpyridin-1-ium,
2-(4-amino-N-(4-(N-(2,5-diethyl)pyrrolophenyl))
phenylazo)-1-ethyl-6-methylpyridin-1-ium,
2-(4-amino-N-(4-(N-(2,5-propyl)pyrrolophenyl))
phenylazo)-1-ethyl-6-methylpyridin-1-ium,
2-(4-amino-N-(4-(N-(2-methyl-5-ethyl)pyrrolophenyl))
phenylazo)-1-ethyl-6-methylpyridin-1-ium,
2-(4-amino-N-(4-(N-(2-methyl-5-propyl)pyrrolophenyl))
phenylazo)-1-ethyl-6-methylpyridin-1-ium,
2-(4-amino-N-(4-(N-(2-methyl-5-phenyl)pyrrolophenyl))
phenylazo)-1-ethyl-6-methylpyridin-1-ium,
2-(4-amino-N-(4-(N-pyrrolophenyl))phenylazo)-1-propyl-6-methylpyridin-1-ium,
2-(4-amino-N-(4-(N-(2,5-dimethyl)pyrrolophenyl))
phenylazo)-1-propyl-6-methylpyridin-1-ium,
2-(4-amino-N-(4-(N-(2,5-diethyl)pyrrolophenyl))
phenylazo)-1-propyl-6-methylpyridin-1-ium,
2-(4-amino-N-(4-(N-(2,5-propyl)pyrrolophenyl))
phenylazo)-1-propyl-6-methylpyridin-1-ium,
2-(4-amino-N-(4-(N-(2-methyl-5-ethyl)pyrrolophenyl))
phenylazo)-1-propyl-6-methylpyridin-1-ium,
2-(4-amino-N-(4-(N-(2-methyl-5-propyl)pyrrolophenyl))
phenylazo)-1-propyl-6-methylpyridin-1-ium,
2-(4-amino-N-(4-(N-(2-methyl-5-phenyl)pyrrolophenyl))
phenylazo)-1-propyl-6-methylpyridin-1-ium,
2-(4-amino-N-(4-(N-pyrrolophenyl))phenylazo)-1-(2-hydroxyethyl)-6-methylpyridin-1-ium,
2-(4-amino-N-(4-(N-(2,5-dimethyl)pyrrolophenyl))
phenylazo)-1-(2-hydroxyethyl)-6-methylpyridin-1-ium,
2-(4-amino-N-(4-(N-(2,5-diethyl)pyrrolophenyl))
phenylazo)-1-(2-hydroxyethyl)-6-methylpyridin-1-ium,
2-(4-amino-N-(4-(N-(2,5-propyl)pyrrolophenyl))
phenylazo)-1-(2-hydroxyethyl)-6-methylpyridin-1-ium,
2-(4-amino-N-(4-(N-(2-methyl-5-ethyl)pyrrolophenyl))
phenylazo)-1-(2-hydroxyethyl)-6-methylpyridin-1-ium,
2-(4-amino-N-(4-(N-(2-methyl-5-propyl)pyrrolophenyl))
phenylazo)-1-(2-hydroxyethyl)-6-methylpyridin-1-ium,
2-(4-amino-N-(4-(N-(2-methyl-5-phenyl)pyrrolophenyl))
phenylazo)-1-(2-hydroxyethyl)-6-methylpyridin-1-ium,
2-(4-amino-N-(4-(N-pyrrolophenyl))phenylazo)-1,4,6-trimethylpyridin-1-ium,
2-(4-amino-N-(4-(N-(2,5-dimethyl)pyrrolophenyl))
phenylazo)-1,4,6-trimethylpyridin-1-ium,
2-(4-amino-N-(4-(N-(2,5-diethyl)pyrrolophenyl))
phenylazo)-1,4,6-trimethylpyridin-1-ium,
2-(4-amino-N-(4-(N-(2,5-propyl)pyrrolophenyl))
phenylazo)-1,4,6-trimethylpyridin-1-ium,
2-(4-amino-N-(4-(N-(2-methyl-5-ethyl)pyrrolophenyl))
phenylazo)-1,4,6-trimethylpyridin-1-ium,
2-(4-amino-N-(4-(N-(2-methyl-5-propyl)pyrrolophenyl))
phenylazo)-1,4,6-trimethylpyridin-1-ium,
2-(4-amino-N-(4-(N-(2-methyl-5-phenyl)pyrrolophenyl))
phenylazo)-1,4,6-trimethylpyridin-1-ium,
2-(4-amino-N-(4-(N-pyrrolophenyl))phenylazo)-1-ethyl-4,6-dimethylpyridin-1-ium,
2-(4-amino-N-(4-(N-(2,5-dimethyl)pyrrolophenyl))
phenylazo)-1-ethyl-4,6-dimethylpyridin-1-ium,
2-(4-amino-N-(4-(N-(2,5-diethyl)pyrrolophenyl))
phenylazo)-1-ethyl-4,6-dimethylpyridin-1-ium,
2-(4-amino-N-(4-(N-(2,5-propyl)pyrrolophenyl))
phenylazo)-1-ethyl-4,6-dimethylpyridin-1-ium,
2-(4-amino-N-(4-(N-(2-methyl-5-ethyl)pyrrolophenyl))
phenylazo)-1-ethyl-4,6-dimethylpyridin-1-ium,
2-(4-amino-N-(4-(N-(2-methyl-5-propyl)pyrrolophenyl))
phenylazo)-1-ethyl-4,6-dimethylpyridin-1-ium,
2-(4-amino-N-(4-(N-(2-methyl-5-phenyl)pyrrolophenyl))
phenylazo)-1-ethyl-4,6-dimethylpyridin-1-ium,
2-(4-amino-N-(4-(N-pyrrolophenyl))phenylazo)-1-propyl-4,6-dimethylpyridin-1-ium,
2-(4-amino-N-(4-(N-(2,5-dimethyl)pyrrolophenyl))
phenylazo)-1-propyl-4,6-dimethylpyridin-1-ium,
2-(4-amino-N-(4-(N-(2,5-diethyl)pyrrolophenyl))
phenylazo)-1-propyl-4,6-dimethylpyridin-1-ium,
2-(4-amino-N-(4-(N-(2,5-propyl)pyrrolophenyl))
phenylazo)-1-propyl-4,6-dimethylpyridin-1-ium,
2-(4-amino-N-(4-(N-(2-methyl-5-ethyl)pyrrolophenyl))
phenylazo)-1-propyl-4,6-dimethylpyridin-1-ium,
2-(4-amino-N-(4-(N-(2-methyl-5-propyl)pyrrolophenyl))
phenylazo)-1-propyl-4,6-dimethylpyridin-1-ium,
2-(4-amino-N-(4-(N-(2-methyl-5-phenyl)pyrrolophenyl))
phenylazo)-1-propyl-4,6-dimethylpyridin-1-ium,
2-(4-amino-N-(4-(N-pyrrolophenyl))phenylazo)-1-(2-hydroxyethyl)-4,6-dimethylpyridin-1-ium,
2-(4-amino-N-(4-(N-(2,5-dimethyl)pyrrolophenyl))
phenylazo)-1-(2-hydroxyethyl)-4,6-dimethylpyridin-1-ium,
2-(4-amino-N-(4-(N-(2,5-diethyl)pyrrolophenyl))
phenylazo)-1-(2-hydroxyethyl)-4,6-dimethylpyridin-1-ium,
2-(4-amino-N-(4-(N-(2,5-propyl)pyrrolophenyl))
phenylazo)-1-(2-hydroxyethyl)-4,6-dimethylpyridin-1-ium,
2-(4-amino-N-(4-(N-(2-methyl-5-ethyl)pyrrolophenyl))
phenylazo)-1-(2-hydroxyethyl)-4,6-dimethylpyridin-1-ium,
2-(4-amino-N-(4-(N-(2-methyl-5-propyl)pyrrolophenyl))
phenylazo)-1-(2-hydroxyethyl)-4,6-dimethylpyridin-1-ium, 2-(4-amino-N-(4-(N-(2-methyl-5-phenyl)pyrrolophenyl))phenylazo)-1-(2-hydroxyethyl)-4,6-dimethylpyridin-1-ium,
2-(4-amino-N-(4-(N-pyrrolophenyl))phenylazo)-1-methyl-2,4-dichloropyridin-1-ium,
2-(4-amino-N-(4-(N-(2,5-dimethyl)pyrrolophenyl))phenylazo)-1-methyl-2,4-dichloropyridin-1-ium,
2-(4-amino-N-(4-(N-(2,5-diethyl)pyrrolophenyl))phenylazo)-1-methyl-2,4-dichloropyridin-1-ium,
2-(4-amino-N-(4-(N-(2,5-propyl)pyrrolophenyl))phenylazo)-1-methyl-2,4-dichloropyridin-1-ium,
2-(4-amino-N-(4-(N-(2-methyl-5-ethyl)pyrrolophenyl))phenylazo)-1-methyl-2,4-dichloropyridin-1-ium,
2-(4-amino-N-(4-(N-(2-methyl-5-propyl)pyrrolophenyl))phenylazo)-1-methyl-2,4-dichloropyridin-1-ium,
2-(4-amino-N-(4-(N-(2-methyl-5-phenyl)pyrrolophenyl))phenylazo)-1-methyl-2,4-dichloropyridin-1-ium,
2-(4-amino-N-(4-(N-pyrrolophenyl))phenylazo)-1-ethyl-2,4-dichloropyridin-1-ium,
2-(4-amino-N-(4-(N-(2,5-dimethyl)pyrrolophenyl))phenylazo)-1-ethyl-2,4-dichloropyridin-1-ium,
2-(4-amino-N-(4-(N-(2,5-diethyl)pyrrolophenyl))phenylazo)-1-ethyl-2,4-dichloropyridin-1-ium,
2-(4-amino-N-(4-(N-(2,5-propyl)pyrrolophenyl))phenylazo)-1-ethyl-2,4-dichloropyridin-1-ium,
2-(4-amino-N-(4-(N-(2-methyl-5-ethyl)pyrrolophenyl))phenylazo)-1-ethyl-2,4-dichloropyridin-1-ium,
2-(4-amino-N-(4-(N-(2-methyl-5-propyl)pyrrolophenyl))phenylazo)-1-ethyl-2,4-dichloropyridin-1-ium,
2-(4-amino-N-(4-(N-(2-methyl-5-phenyl)pyrrolophenyl))phenylazo)-1-ethyl-2,4-dichloropyridin-1-ium,
2-(4-amino-N-(4-(N-pyrrolophenyl))phenylazo)-1-propyl-2,4-dichloropyridin-1-ium,
2-(4-amino-N-(4-(N-(2,5-dimethyl)pyrrolophenyl))phenylazo)-1-propyl-2,4-dichloropyridin-1-ium,
2-(4-amino-N-(4-(N-(2,5-diethyl)pyrrolophenyl))phenylazo)-1-propyl-2,4-dichloropyridin-1-ium,
2-(4-amino-N-(4-(N-(2,5-propyl)pyrrolophenyl))phenylazo)-1-propyl-2,4-dichloropyridin-1-ium,
2-(4-amino-N-(4-(N-(2-methyl-5-ethyl)pyrrolophenyl))phenylazo)-1-propyl-2,4-dichloropyridin-1-ium,
2-(4-amino-N-(4-(N-(2-methyl-5-propyl)pyrrolophenyl))phenylazo)-1-propyl-2,4-dichloropyridin-1-ium,
2-(4-amino-N-(4-(N-(2-methyl-5-phenyl)pyrrolophenyl))phenylazo)-1-propyl-2,4-dichloropyridin-1-ium,
2-(4-amino-N-(4-(N-pyrrolophenyl))phenylazo)-1-(2-hydroxyethyl)-2,4-dichloropyridin-1-ium,
2-(4-amino-N-(4-(N-(2,5-dimethyl)pyrrolophenyl))phenylazo)-1-(2-hydroxyethyl)-2,4-dichloropyridin-1-ium,
2-(4-amino-N-(4-(N-(2,5-diethyl)pyrrolophenyl))phenylazo)-1-(2-hydroxyethyl)-2,4-dichloropyridin-1-ium,
2-(4-amino-N-(4-(N-(2,5-propyl)pyrrolophenyl))phenylazo)-1-(2-hydroxyethyl)-2,4-dichloropyridin-1-ium,
2-(4-amino-N-(4-(N-(2-methyl-5-ethyl)pyrrolophenyl))phenylazo)-1-(2-hydroxyethyl)-2,4-dichloropyridin-1-ium,
2-(4-amino-N-(4-(N-(2-methyl-5-propyl)pyrrolophenyl))phenylazo)-1-(2-hydroxyethyl)-2,4-dichloropyridin-1-ium,
2-(4-amino-N-(4-(N-(2-methyl-5-phenyl)pyrrolophenyl))phenylazo)-1-(2-hydroxyethyl)-2,4-dichloropyridin-1-ium,
2-(4-amino-N-(4-(N-pyrrolophenyl))phenylazo)-1-methyl-5-chloropyridin-1-ium,
2-(4-amino-N-(4-(N-(2,5-dimethyl)pyrrolophenyl))phenylazo)-1-methyl-5-chloropyridin-1-ium,
2-(4-amino-N-(4-(N-(2,5-diethyl)pyrrolophenyl))phenylazo)-1-methyl-5-chloropyridin-1-ium,
2-(4-amino-N-(4-(N-(2,5-propyl)pyrrolophenyl))phenylazo)-1-methyl-5-chloropyridin-1-ium,
2-(4-amino-N-(4-(N-(2-methyl-5-ethyl)pyrrolophenyl))phenylazo)-1-methyl-5-chloropyridin-1-ium,
2-(4-amino-N-(4-(N-(2-methyl-5-propyl)pyrrolophenyl))phenylazo)-1-methyl-5-chloropyridin-1-ium,
2-(4-amino-N-(4-(N-(2-methyl-5-phenyl)pyrrolophenyl))phenylazo)-1-methyl-5-chloropyridin-1-ium,
2-(4-amino-N-(4-(N-pyrrolophenyl))phenylazo)-1-ethyl-5-chloropyridin-1-ium,
2-(4-amino-N-(4-(N-(2,5-dimethyl)pyrrolophenyl))phenylazo)-1-ethyl-5-chloropyridin-1-ium,
2-(4-amino-N-(4-(N-(2,5-diethyl)pyrrolophenyl))phenylazo)-1-ethyl-5-chloropyridin-1-ium,
2-(4-amino-N-(4-(N-(2,5-propyl)pyrrolophenyl))phenylazo)-1-ethyl-5-chloropyridin-1-ium,
2-(4-amino-N-(4-(N-(2-methyl-5-ethyl)pyrrolophenyl))phenylazo)-1-ethyl-5-chloropyridin-1-ium,
2-(4-amino-N-(4-(N-(2-methyl-5-propyl)pyrrolophenyl))phenylazo)-1-ethyl-5-chloropyridin-1-ium,
2-(4-amino-N-(4-(N-(2-methyl-5-phenyl)pyrrolophenyl))phenylazo)-1-ethyl-5-chloropyridin-1-ium,
2-(4-amino-N-(4-(N-pyrrolophenyl))phenylazo)-1-propyl-5-chloropyridin-1-ium,
2-(4-amino-N-(4-(N-(2,5-dimethyl)pyrrolophenyl))phenylazo)-1-propyl-5-chloropyridin-1-ium,
2-(4-amino-N-(4-(N-(2,5-diethyl)pyrrolophenyl))phenylazo)-1-propyl-5-chloropyridin-1-ium,
2-(4-amino-N-(4-(N-(2,5-propyl)pyrrolophenyl))phenylazo)-1-propyl-5-chloropyridin-1-ium,
2-(4-amino-N-(4-(N-(2-methyl-5-ethyl)pyrrolophenyl))phenylazo)-1-propyl-5-chloropyridin-1-ium,
2-(4-amino-N-(4-(N-(2-methyl-5-propyl)pyrrolophenyl))phenylazo)-1-propyl-5-chloropyridin-1-ium,
2-(4-amino-N-(4-(N-(2-methyl-5-phenyl)pyrrolophenyl))phenylazo)-1-propyl-5-chloropyridin-1-ium,
2-(4-amino-N-(4-(N-pyrrolophenyl))phenylazo)-1-(2-hydroxyethyl)-5-chloropyridin-1-ium,
2-(4-amino-N-(4-(N-(2,5-dimethyl)pyrrolophenyl))phenylazo)-1-(2-hydroxyethyl)-5-chloropyridin-1-ium,
2-(4-amino-N-(4-(N-(2,5-diethyl)pyrrolophenyl))phenylazo)-1-(2-hydroxyethyl)-5-chloropyridin-1-ium,
2-(4-amino-N-(4-(N-(2,5-propyl)pyrrolophenyl))phenylazo)-1-(2-hydroxyethyl)-5-chloropyridin-1-ium,
2-(4-amino-N-(4-(N-(2-methyl-5-ethyl)pyrrolophenyl))phenylazo)-1-(2-hydroxyethyl)-5-chloropyridin-1-ium,
2-(4-amino-N-(4-(N-(2-methyl-5-propyl)pyrrolophenyl))phenylazo)-1-(2-hydroxyethyl)-5-chloropyridin-1-ium,
2-(4-amino-N-(4-(N-(2-methyl-5-phenyl)pyrrolophenyl))phenylazo)-1-(2-hydroxyethyl)-5-chloropyridin-1-ium,
2-(4-amino-N-(4-(N-pyrrolophenyl))phenylazo)-1-methyl-3-hydroxypyridin-1-ium,
2-(4-amino-N-(4-(N-(2,5-dimethyl)pyrrolophenyl))phenylazo)-1-methyl-3-hydroxypyridin-1-ium,
2-(4-amino-N-(4-(N-(2,5-diethyl)pyrrolophenyl))phenylazo)-1-methyl-3-hydroxypyridin-1-ium,
2-(4-amino-N-(4-(N-(2,5-propyl)pyrrolophenyl))phenylazo)-1-methyl-3-hydroxypyridin-1-ium,
2-(4-amino-N-(4-(N-(2-methyl-5-ethyl)pyrrolophenyl))phenylazo)-1-methyl-3-hydroxypyridin-1-ium,
2-(4-amino-N-(4-(N-(2-methyl-5-propyl)pyrrolophenyl))phenylazo)-1-methyl-3-hydroxypyridin-1-ium,
2-(4-amino-N-(4-(N-(2-methyl-5-phenyl)pyrrolophenyl))phenylazo)-1-methyl-3-hydroxypyridin-1-ium, 2-(4-amino-N-(4-(N-pyrrolophenyl))phenylazo)-1-ethyl-3-hydroxypyridin-1-ium,
2-(4-amino-N-(4-(N-(2,5-dimethyl)pyrrolophenyl))phenylazo)-1-ethyl-3-hydroxypyridin-1-ium,
2-(4-amino-N-(4-(N-(2,5-diethyl)pyrrolophenyl))phenylazo)-1-ethyl-3-hydroxypyridin-1-ium,
2-(4-amino-N-(4-(N-(2,5-propyl)pyrrolophenyl))phenylazo)-1-ethyl-3-hydroxypyridin-1-ium,
2-(4-amino-N-(4-(N-(2-methyl-5-ethyl)pyrrolophenyl))phenylazo)-1-ethyl-3-hydroxypyridin-1-ium,
2-(4-amino-N-(4-(N-(2-methyl-5-propyl)pyrrolophenyl))phenylazo)-1-ethyl-3-hydroxypyridin-1-ium,
2-(4-amino-N-(4-(N-(2-methyl-5-phenyl)pyrrolophenyl))phenylazo)-1-ethyl-3-hydroxypyridin-1-ium,
2-(4-amino-N-(4-(N-pyrrolophenyl))phenylazo)-1-propyl-3-hydroxypyridin-1-ium,
2-(4-amino-N-(4-(N-(2,5-dimethyl)pyrrolophenyl))phenylazo)-1-propyl-3-hydroxypyridin-1-ium,
2-(4-amino-N-(4-(N-(2,5-diethyl)pyrrolophenyl))phenylazo)-1-propyl-3-hydroxypyridin-1-ium,
2-(4-amino-N-(4-(N-(2,5-propyl)pyrrolophenyl))phenylazo)-1-propyl-3-hydroxypyridin-1-ium,
2-(4-amino-N-(4-(N-(2-methyl-5-ethyl)pyrrolophenyl))phenylazo)-1-propyl-3-hydroxypyridin-1-ium,
2-(4-amino-N-(4-(N-(2-methyl-5-propyl)pyrrolophenyl))phenylazo)-1-propyl-3-hydroxypyridin-1-ium,
2-(4-amino-N-(4-(N-(2-methyl-5-phenyl)pyrrolophenyl))phenylazo)-1-propyl-3-hydroxypyridin-1-ium,
2-(4-amino-N-(4-(N-pyrrolophenyl))phenylazo)-1-(2-hydroxyethyl)-3-hydroxypyridin-1-ium,
2-(4-amino-N-(4-(N-(2,5-dimethyl)pyrrolophenyl))phenylazo)-1-(2-hydroxyethyl)-3-hydroxypyridin-1-ium,
2-(4-amino-N-(4-(N-(2,5-diethyl)pyrrolophenyl))phenylazo)-1-(2-hydroxyethyl)-3-hydroxypyridin-1-ium,
2-(4-amino-N-(4-(N-(2,5-propyl)pyrrolophenyl))phenylazo)-1-(2-hydroxyethyl)-3-hydroxypyridin-1-ium,
2-(4-amino-N-(4-(N-(2-methyl-5-ethyl)pyrrolophenyl))phenylazo)-1-(2-hydroxyethyl)-3-hydroxypyridin-1-ium,
2-(4-amino-N-(4-(N-(2-methyl-5-propyl)pyrrolophenyl))phenylazo)-1-(2-hydroxyethyl)-3-hydroxypyridin-1-ium,
2-(4-amino-N-(4-(N-(2-methyl-5-phenyl)pyrrolophenyl))phenylazo)-1-(2-hydroxyethyl)-3-hydroxypyridin-1-ium,
2-(4-amino-N-(4-(N-imidazolophenyl))phenylazo)-1-methylpyridin-1-ium,
2-(4-amino-N-(4-(N-imidazolophenyl))phenylazo)-1-ethylpyridin-1-ium,
2-(4-amino-N-(4-(N-imidazolophenyl))phenylazo)-1-propylpyridin-1-ium,
2-(4-amino-N-(4-(N-imidazolophenyl))phenylazo)-1-(2-hydroxyethyl)pyridin-1-ium,
2-(4-amino-N-(4-(N-imidazolophenyl))phenylazo)-1,3-dimethylpyridin-1-ium,
2-(4-amino-N-(4-(N-imidazolophenyl))phenylazo)-1,4-dimethylpyridin-1-ium,
2-(4-amino-N-(4-(N-imidazolophenyl))phenylazo)-1,5-dimethylpyridin-1-ium,
2-(4-amino-N-(4-(N-imidazolophenyl))phenylazo)-1,6-dimethylpyridin-1-ium,
2-(4-amino-N-(4-(N-imidazolophenyl))phenylazo)-1,4,6-trimethylpyridin-1-ium,
2-(4-amino-N-(4-(N-imidazolophenyl))phenylazo)-1,6-dimethylpyridin-1-ium,
2-(4-amino-N-(4-(N-imidazolophenyl))phenylazo)-1-methyl-2,4-dichloropyridin-1-ium,
2-(4-amino-N-(4-(N-imidazolophenyl))phenylazo)-1-methyl-5-chloropyridin-1-ium,
2-(4-amino-N-(4-(N-imidazolophenyl))phenylazo)-1-ethyl-3-methylpyridin-1-ium,
2-(4-amino-N-(4-(N-imidazolophenyl))phenylazo)-1-ethyl-4-methylpyridin-1-ium,
2-(4-amino-N-(4-(N-imidazolophenyl))phenylazo)-1-ethyl-5-methylpyridin-1-ium,
2-(4-amino-N-(4-(N-imidazolophenyl))phenylazo)-1-ethyl-6-methylpyridin-1-ium,
2-(4-amino-N-(4-(N-imidazolophenyl))phenylazo)-1-ethyl-4,6-dimethylpyridin-1-ium,
2-(4-amino-N-(4-(N-imidazolophenyl))phenylazo)-1-ethyl-6-methylpyridin-1-ium,
2-(4-amino-N-(4-(N-imidazolophenyl))phenylazo)-1-ethyl-2,4-dichloropyridin-1-ium,
2-(4-amino-N-(4-(N-imidazolophenyl))phenylazo)-1-ethyl-5-chloropyridin-1-ium,
2-(4-amino-N-(4-(N-imidazolophenyl))phenylazo)-1-propyl-3-methylpyridin-1-ium,
2-(4-amino-N-(4-(N-imidazolophenyl))phenylazo)-1-propyl-4-methylpyridin-1-ium,
2-(4-amino-N-(4-(N-imidazolophenyl))phenylazo)-1-propyl-5-methylpyridin-1-ium,
2-(4-amino-N-(4-(N-imidazolophenyl))phenylazo)-1-propyl-6-methylpyridin-1-ium,
2-(4-amino-N-(4-(N-imidazolophenyl))phenylazo)-1-propyl-4,6-dimethylpyridin-1-ium,
2-(4-amino-N-(4-(N-imidazolophenyl))phenylazo)-1-propyl-6-methylpyridin-1-ium,
2-(4-amino-N-(4-(N-imidazolophenyl))phenylazo)-1-propyl-2,4-dichloropyridin-1-ium,
2-(4-amino-N-(4-(N-imidazolophenyl))phenylazo)-1-propyl-5-chloropyridin-1-ium,
2-(4-amino-N-(4-(N-imidazolophenyl))phenylazo)-1-(2-hydroxyethyl)-3-methylpyridin-1-ium,
2-(4-amino-N-(4-(N-imidazolophenyl))phenylazo)-1-(2-hydroxyethyl)-4-methylpyridin-1-ium,
2-(4-amino-N-(4-(N-imidazolophenyl))phenylazo)-1-(2-hydroxyethyl)-5-methylpyridin-1-ium,
2-(4-amino-N-(4-(N-imidazolophenyl))phenylazo)-1-(2-hydroxyethyl)-6-methylpyridin-1-ium,
2-(4-amino-N-(4-(N-imidazolophenyl))phenylazo)-1-(2-hydroxyethyl)-4,6-dimethylpyridin-1-ium,
2-(4-amino-N-(4-(N-imidazolophenyl))phenylazo)-1-(2-hydroxyethyl)-6-methylpyridin-1-ium,
2-(4-amino-N-(4-(N-imidazolophenyl))phenylazo)-1-(2-hydroxyethyl)-2,4-dichloropyridin-1-ium,
2-(4-amino-N-(4-(N-imidazolophenyl))phenylazo)-1-(2-hydroxyethyl)-5-chloropyridin-1-ium.

According to an aspect of the disclosure, mention may be made, for instance, of the following dyes of formula (I):
2-(4-amino-N-(4-(N-pyrrolophenyl))phenylazo)-1,3-dimethyl-3H-imidazol-1-ium,
2-(4-amino-N-(4-(N-(2,5-dimethyl)pyrrolophenyl))phenylazo)-1,3-dimethyl-3H-imidazol-1-ium,
2-(4-amino-N-(4-(N-(2-methyl-5-propyl)pyrrolophenyl))phenylazo)-1,3-dimethyl-3H-imidazol-1-ium,
2-(4-amino-N-(4-(N-(2-methyl-5-phenyl)pyrrolophenyl))phenylazo)-1,3-dimethyl-3H-imidazol-1-ium,
2-(4-amino-N-(4-(N-[2-methyl-3-carboxyethyl-5-(4-chlorophenyl)pyrrolophenyl]]phenylazo)-1,3-dimethyl-3H-imidazol-1-ium,
wherein each of these dyes is in combination with an anion $X^-$ defined above.

The concentration of monocationic monoazo dye of formula (I) in composition can vary in an amount ranging from approximately 0.001 to 5% by weight with respect to the total weight of the dyeing composition, for example from approximately 0.05 to 2%.

The dyeing composition according to the disclosure can additionally comprise at least one direct dye other than those of formula (I), it being possible for these dyes to be chosen from neutral, acidic, and cationic direct nitrobenzene dyes, neutral, acidic, and cationic direct azo dyes, neutral, acidic, and cationic direct quinone dyes and, for instance, anthraquinone dyes, direct azine dyes, direct methine dyes, direct tetraazapentamethine dyes, direct triarylmethane dyes, direct indoamine dyes, and direct natural dyes.

Mention may be made, among direct nitrobenzene dyes, of the following compounds:
1,4-diamino-2-nitrobenzene,
1-amino-2-nitro-4-(β-hydroxyethylamino)benzene,
1-amino-2-nitro-4-[bis(β-hydroxyethyl)amino]benzene,
1,4-bis(β-hydroxyethylamino)-2-nitrobenzene,
1-(β-hydroxyethylamino)-2-nitro-4-[bis(β-hydroxyethyl) amino]benzene,
1-(β-hydroxyethylamino)-2-nitro-4-aminobenzene,
1-(β-hydroxyethylamino)-2-nitro-4-[(ethyl)(β-hydroxyethyl)amino]benzene,
1-amino-3-methyl-4-(β-hydroxyethylamino)-6-nitrobenzene,
1-amino-2-nitro-4-(β-hydroxyethylamino)-5-chlorobenzene,
1,2-diamino-4-nitrobenzene,
1-amino-2-(β-hydroxyethylamino)-5-nitrobenzene,
1,2-bis(β-hydroxyethylamino)-4-nitrobenzene,
1-amino-2-[tris(hydroxymethyl)methylamino]-5-nitrobenzene,
1-hydroxy-2-amino-5-nitrobenzene,
1-hydroxy-2-amino-4-nitrobenzene,
1-hydroxy-3-nitro-4-aminobenzene,
1-hydroxy-2-amino-4,6-dinitrobenzene,
1-(β-hydroxyethyloxy)-2-(β-hydroxyethylamino)-5-nitrobenzene,
1-methoxy-2-(β-hydroxyethylamino)-5-nitrobenzene,
1-(β-hydroxyethyloxy)-3-methylamino-4-nitrobenzene,
1-(β,γ-dihydroxypropyloxy)-3-methylamino-4-nitrobenzene,
1-(β-hydroxyethylamino)-4-(β,γ-dihydroxypropyloxy)-2-nitrobenzene,
1-(β,γ-dihydroxypropylamino)-4-trifluoromethyl-2-nitrobenzene,
1-(β-hydroxyethylamino)-4-trifluoromethyl-2-nitrobenzene,
1-(β-hydroxyethylamino)-3-methyl-2-nitrobenzene,
1-(β-aminoethylamino)-5-methoxy-2-nitrobenzene,
1-hydroxy-2-chloro-6-ethylamino-4-nitrobenzene,
1-hydroxy-2-chloro-6-amino-4-nitrobenzene,
1-hydroxy-6-[bis(β-hydroxyethyl)amino]-3-nitrobenzene,
1-(β-hydroxyethylamino)-2-nitrobenzene,
1-hydroxy-4-(β-hydroxyethylamino)-3-nitrobenzene.

Mention may be made, among direct azo dyes, of the cationic azo dyes disclosed in Patent Applications WO 95/15144, WO 95/01772 and EP 714 954, the content of which forms a part of the disclosure.
Mention may also be made, among these compounds, of the following dyes:
1,3-dimethyl-2-[[4-(dimethylamino)phenyl]azo]-1H-imidazolium chloride,
1,3-dimethyl-2-[(4-aminophenyl)azo]-1H-imidazolium chloride,
1-methyl-4-[(methylphenylhydrazono)methyl]pyridinium methyl sulphate.

Mention may further be made, among direct azo dyes, for example, of the following dyes, described in the Colour Index International, 3$^{rd}$ edition:

Disperse Red 17,
Acid Yellow 9,
Acid Black 1,
Basic Red 22,
Basic Red 76,
Basic Yellow 57,
Basic Brown 16,
Acid Yellow 36,
Acid Orange 7,
Acid Red 33,
Acid Red 35,
Basic Brown 17,
Acid Yellow 23,
Acid Orange 24,
Disperse Black 9.

Mention may also be made of 1-(4'-aminodiphenylazo)-2-methyl-4-[bis(β-hydroxyethyl)amino]benzene and 4-hydroxy-3-(2-methoxyphenylazo)-1-naphthalenesulphonic acid.

Mention may be made, among direct quinone dyes, for instance, of the following dyes:
Disperse Red 15,
Solvent Violet 13,
Acid Violet 43,
Disperse Violet 1,
Disperse Violet 4,
Disperse Blue 1,
Disperse Violet 8,
Disperse Blue 3,
Disperse Red 11,
Acid Blue 62,
Disperse Blue 7,
Basic Blue 22,
Disperse Violet 15,
Basic Blue 99,
and of the following compounds:
1-(N-methylmorpholiniumpropylamino)-4-hydroxyanthraquinone,
1-aminopropylamino-4-(methylamino)anthraquinone,
1-(aminopropylamino)anthraquinone,
5-(β-hydroxyethyl)-1,4-diaminoanthraquinone,
2-(aminoethylamino)anthraquinone,
1,4-bis(β,γ-dihydroxypropylamino)anthraquinone.

Mention may be made, among azine dyes, of the following compounds:
Basic Blue 17
Basic Red 2.

Mention may be made, among direct tetraazapentamethine dyes, of the following compounds:

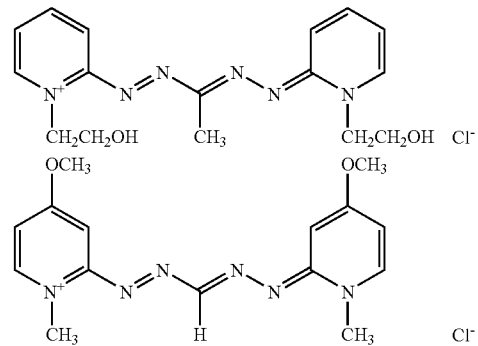

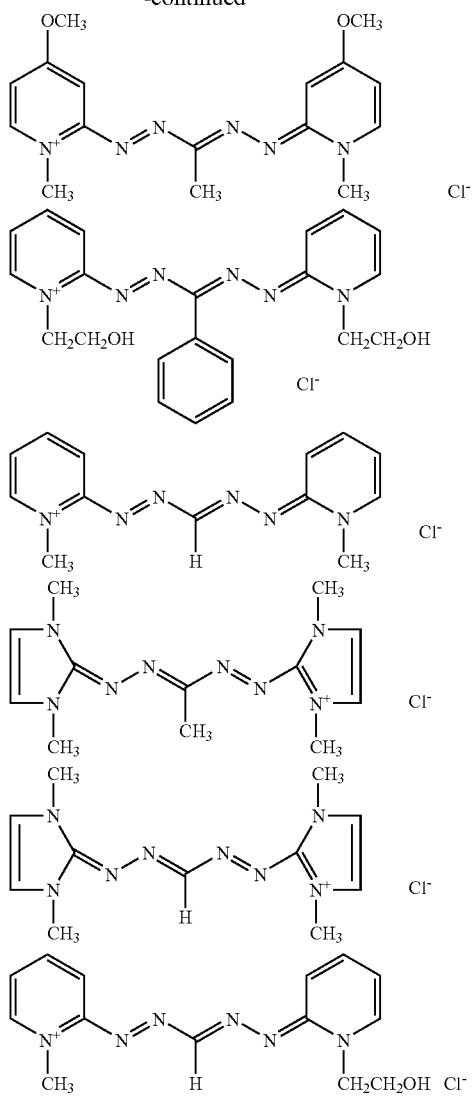

Mention may be made, among triarylmethane dyes, of the following compounds
Basic Green 1,
Acid Blue 9,
Basic Violet 3,
Basic Violet 14,
Basic Blue 7,
Acid Violet 49,
Basic Blue 26,
Acid Blue 7.

Mention may be made, among indoamine dyes, of the following compounds:
2-(β-hydroxyethylamino)-5-[bis(β-4'-hydroxyethyl)amino]anilino-1,4-benzoquinone,
2-(β-hydroxyethylamino)-5-(2'-methoxy-4'-aminoanilino)-1,4-benzoquinone,
3-[N-(2'-chloro-4'-hydroxyphenyl)acetylamino]-6-methoxy-1,4-benzquinone imine,
3-[N-(3'-chloro-4'-(methylamino)phenyl)ureido]-6-methyl-1,4-benzoquinone imine,
3-[[4'-[N-(ethyl,carbamoylmethyl)amino]phenyl]-ureido]-6-methyl-1,4-benzoquinone imine.

Mention may be made, among direct natural dyes which can be used according to the disclosure, of lawsone, juglone, alizarin, purpurin, carminic acid, kermesic acid, purpurogallin, protocatechualdehyde, indigo, isatin, curcumin, spinulosin or apigenidin. Use may also be made of the extracts or decoctions comprising these natural dyes and for instance, cataplasms or henna-based extracts.

The additional direct dye or dyes may represent from 0.001 to 20% by weight approximately of the total weight of the composition and, for example, from 0.005 to 10% by weight approximately.

The composition of the disclosure can additionally comprise an oxidizing agent. This oxidizing agent can be any oxidizing agent conventionally used for the bleaching of human keratinous fibres. The oxidizing agent may be chosen from hydrogen peroxide, urea hydrogen peroxide, alkali metal bromates, persalts, such as perborates and persulfates, peracids and enzymes, among which may be mentioned peroxidases, 2-electron oxidoreductases, such as uricases, and 4-electron oxygenases, such as laccases. The use of hydrogen peroxide is a suitable example.

When the composition according to the disclosure is intended for conventional oxidation dyeing, it can additionally comprise an oxidation base. This oxidation base may be chosen from the oxidation bases conventionally used in oxidation dyeing, for example para-phenylenediamines, bisphenylalkylenediamines, para-aminophenols, ortho-aminophenols and heterocyclic bases.

Mention may be made, among para-phenylenediamines, by way of example, of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-(β-hydroxyethyl)-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl, β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine, 2-(β-acetylaminoethyloxy)-para-phenylenediamine, N-(β-methoxyethyl)-para-phenylenediamine, 4-(aminophenyl)pyrrolidine, 2-thienyl-para-phenylenediamine, 2-(β-hydroxyethylamino)-5-aminotoluene, and their addition salts with an acid.

Among the para-phenylenediamines mentioned above, para-phenylenediamine, para-tolylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-(β-acetylaminoethyloxy)-para-phenylenediamine, and their addition salts with an acid, may be mentioned.

Mention may be made, among bisphenylalkylenediamines, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)

tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, and their addition salts with an acid.

Mention may be made, among para-aminophenols, by way of example, of para-aminophenol, 4-amino-3-methylphenol, 4-amino-3-fluorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-(2-aminomethyl)phenol, 4-amino-2-[(β-hydroxyethyl)aminomethyl]phenol, 4-amino-2-fluorophenol, and their addition salts with an acid.

Mention may be made, among ortho-aminophenols, by way of example, of 2-aminophenol, 2-amino-5-methylphenol, 2-amino-6-methylphenol, 5-acetamido-2-aminophenol, and their addition salts with an acid.

Mention may be made, among heterocyclic bases, by way of example, of pyridine derivatives, pyrimidine derivatives, and pyrazole derivatives.

Mention may be made, among pyridine derivatives, of the compounds disclosed, for example, in Patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and their addition salts with an acid.

Mention may be made, among pyrimidine derivatives, of the compounds disclosed, for example, in Patents DE 2 359 399, JP 88-169 571, JP 05 163 124 or EP 0 770 375 or Patent Application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine or 2,5,6-triaminopyrimidine, and pyrazolopyrimidine derivatives, such as those mentioned in Patent Application FR-A-2 750 048, among which may be mentioned pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-(imidazolylpropylamino)pyrazolo[1,5-a]pyrimidine, and their addition salts with an acid and their tautomeric forms, when a tautomeric equilibrium exists.

Mention may be made, among pyrazole derivatives, of the compounds disclosed in Patents DE 3 843 892 and DE 4 133 957 and Patent Applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-(hydroxymethyl)pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-(methylamino)pyrazole, 3,5-diamino-4-(β-hydroxyethyl)amino-1-methylpyrazole, and their addition salts with an acid.

The composition according to the disclosure can additionally comprise one or more couplers conventionally used for the conventional oxidation dyeing of human keratinous fibres. Mention may be made, among these couplers, of meta-phenylenediamines, meta-aminophenols, meta-diphenols, naphthalene couplers, and heterocyclic couplers.

Mention may be made, by way of example, of 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-(β-hydroxyethylamino)-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, and their addition salts with an acid.

In the composition of the present disclosure, the at least one coupler, when present, may generally be present in an amount ranging from 0.001 to 10% by weight approximately of the total weight of the dyeing composition, for instance from 0.005 to 6%. The oxidation base or bases can be present in an amount ranging from 0.001 to 10% by weight approximately of the total weight of the dyeing composition, for instance from 0.005 to 6%.

Generally, the addition salts with an acid that can be used in the context of the dyeing compositions of the disclosure for the oxidation bases and the couplers are chosen from hydrochlorides, hydrobromides, sulphates, citrates, succinates, tartrates, lactates, tosylates, benzenesulphonates, phosphates, and acetates.

The medium cosmetically acceptable for dyeing, also referred to as dyeing support, is generally composed of water or of a mixture of water and of at least one organic solvent, in order to dissolve the compounds which would not be sufficiently soluble in water. Mention may be made, as organic solvents, for example, of lower $C_1$–$C_4$ alkanols, such as ethanol and isopropanol; polyols and polyol ethers, such as 2-butoxyethanol, propylene glycol, propylene glycol monomethyl ether, diethylene glycol monoethyl ether and diethylene glycol monomethyl ether; and aromatic alcohols, such as benzyl alcohol or phenoxyethanol; and their mixtures.

The solvents can be present in amounts ranging from 1 to 40% by weight approximately with respect to the total weight of the dyeing composition, for instance from 5 to 30% by weight approximately.

The dyeing composition in accordance with the present disclosure can also include at least one of various adjuvants conventionally used in hair dyeing compositions, such as anionic, cationic, nonionic, amphoteric or zwitterionic surface-active agents or their mixtures, anionic, cationic, nonionic, amphoteric or zwitterionic polymers or their mixtures, inorganic or organic thickening agents, for example anionic, cationic, nonionic and amphoteric associative polymer thickeners, antioxidants, penetration agents, sequestering agents, fragrances, buffers, dispersing agents, conditioning agents, such as, for example, volatile or non-volatile and modified or unmodified silicones, film-forming agents, ceramides, preservatives or opacifying agents.

These above adjuvants can be generally present in an amount, for each of them, ranging from 0.01 to 20% by weight with respect to the weight of the composition.

Of course, a person skilled in the art will take care to choose the optional additional compounds so that at least one of the beneficial properties intrinsically attached to the dyeing composition in accordance with the disclosure is not, or not substantially, detrimentally affected by the envisaged addition or additions.

The pH of the dyeing composition in accordance with the disclosure generally ranges from 3 to 12 approximately, for instance from 5 to 11 approximately. It can be adjusted to the desired value by means of acidifying or basifying agents commonly used in dyeing keratinous fibres or alternatively using conventional buffer systems.

Mention may be made, among acidifying agents, by way of example, of inorganic or organic acids, such as hydrochloric acid, orthophosphoric acid, sulphuric acid, carboxylic acids, such as acetic acid, tartaric acid, citric acid, lactic acid, and sulphonic acids.

Mention may be made, among basifying agents, by way of example, of ammonia, alkaline carbonates, alkanolamines, such as mono-, di- and triethanolamines, and their derivatives, sodium hydroxide, potassium hydroxide and the compounds of formula (VI):

(VI)

wherein W is a propylene residue optionally substituted by at least one entity chosen from hydroxyl groups and $C_1$–$C_4$ alkyl radicals and wherein $R_{16}$, $R_{17}$, $R_{18}$ and $R_{19}$, which may be identical or different, can be chosen from hydrogen atoms $C_1$–$C_4$ alkyl radicals, and $C_1$–$C_4$ hydroxyalkyl radicals.

The dyeing composition according to the disclosure can be provided in various forms, such as in the form of liquids, creams, or gels, or in any other form appropriate for carrying out dyeing of human keratinous fibres, for example the hair.

Another embodiment of the disclosure is a direct dyeing process which comprises the application of a dyeing composition comprising a dye of formula (I) as defined above to human keratinous fibres. After a leave-in time, the fibres are rinsed, allowing coloured fibres to appear.

The application to the fibres of the dyeing composition comprising the monocationic monoazo dye of formula (I) may, if desired, be carried out in the presence of an oxidizing agent which brings about the bleaching of the fibre (the dyeing process then constitutes a lightening direct dyeing process). This oxidizing agent can be added to the composition comprising the dye of formula (I) at the time of use or applied directly to the fibre.

Another aspect of the present disclosure is an oxidation dyeing process which comprises the application to human keratinous fibres of a dyeing composition which comprises a dye of formula (I), at least one oxidation base and optionally at least one coupler, in the presence of an oxidizing agent, wherein the oxidation base, the coupler and the oxidizing agent are as defined above.

The colour can be developed at acidic, neutral or alkaline pH and the oxidizing agent can be added to the composition of the disclosure either at the time of use or it can be employed from an oxidizing composition comprising it, applied to the fibres simultaneously with or sequentially to the dyeing composition.

In the case of oxidation dyeing or of lightening direct dyeing, the dyeing composition is mixed, for example at the time of use, with a composition comprising, in a cosmetically acceptable medium, at least one oxidizing agent, this oxidizing agent being present in an amount sufficient to develop a colouring. The mixture obtained is subsequently applied to the fibres. After a leave-in time of 3 to 50 minutes approximately, for example 5 to 30 minutes approximately, the fibres are rinsed, washed with a shampoo, rinsed again and then dried.

The oxidizing composition can also include various adjuvants conventionally used in hair dyeing compositions and as defined above.

The pH of the oxidizing composition that includes the oxidizing agent is such that, after mixing with the dyeing composition, the pH of the resulting composition applied to human keratinous fibres may range from 3 to 12 approximately, for example from 5 to 11. It can be adjusted to the desired value by means of acidifying or basifying agents commonly used in dyeing human keratinous fibres and as defined above.

The composition which is finally applied to the fibres can be provided in various forms, such as in the form of liquids, creams or gels or in any other form appropriate for carrying out dyeing of human keratinous fibres, such as the hair.

Another embodiment of the disclosure is a multi-compartment device or dyeing 'kit' wherein at least one compartment includes the dyeing composition of the disclosure and at least one other compartment includes the oxidizing composition. This device or kit can be equipped with a means allowing the desired mixture to be delivered to the hair, such as the devices disclosed in Patent FR 2 586 913.

Still another embodiment of the disclosure is the use of the monocationic monoazo dyes of formula (I) as direct dyes in, or for the preparation of, a composition for the dyeing of human keratinous fibres, for example the hair.

Another embodiment of the disclosure is the monocationic monoazo dyes of formula (I) as defined above and for which, when $W_5$ denotes imidazole and when $W_1$ denotes benzimidazole, $W_3$ is other than hydrogen if $W_4$ denotes phenyl (benzimidazole, that is to say that $Z_1=NR_2$, $R_1=R_2=CH_3$, $Z_2=CR_4$, $Z_3=CR_{13}$ and $R_4$ with $R_{13}$ together form a phenyl radical).

Another embodiment of the disclosure is the monocationic monoazo dyes of formula (I) as defined above and wherein:

$W_1$ is chosen from 5- and 6-membered cationic aromatic heterocycles of formulae (II) and (III):

Formula (II)

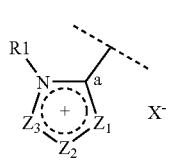

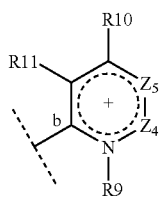

wherein:
- $Z_1$ is chosen from an oxygen atom, a sulphur atom, $NR_2$ radicals, and $CR_3$ radicals,
- $Z_2$ is chosen from a nitrogen atom and $CR_4$ radicals,
- $Z_3$ is chosen from $NR_{12}$ radicals and $CR_{13}$ radicals,
- $Z_4$ is chosen from a nitrogen atom and $CR_{14}$ radicals,
- $Z_5$ is chosen from a nitrogen atom and $CR_{15}$ radicals,
- with the proviso that formulae (II) and (III) do not comprise more than two adjacent heteroatoms;
- the bond a connects the 5-membered cationic ring of formula (II) to the azo functional group of the formula (I),
- the bond b connects the 6-membered cationic ring of formula (III) to the azo functional group of the formula (I),
- $X^-$ is chosen from organic and inorganic anions,
- $W_2$ and $W_4$ (formula I), which may be identical or different, are chosen from divalent carbonaceous aromatic groups and pyridine groups of formulae (IV) and (V):

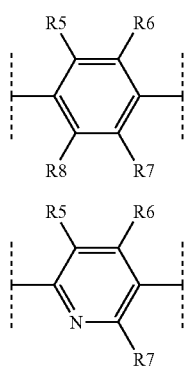

- $W_3$ is chosen from a hydrogen atom and $C_1$–$C_6$ alkyl radicals, which may optionally be substituted with at least one radical chosen from hydroxyl radicals, alkoxy radicals, amino radicals, mono($C_1$–$C_4$)alkylamino radicals, and di($C_1$–$C_4$)alkylamino radicals,
- $W_5$ is chosen from 5-membered nitrogenous heteroaromatic radicals connected to $W_4$ via the nitrogen atom of the ring of the said heteroaromatic radical, wherein the heteroaromatic radical is chosen from pyrazolyl, pyrrolyl, imidazolyl, triazolyl and thiadiazolyl radicals, it being possible for each of these heteroaromatic radicals to be substituted by at least one entity chosen from hydrogen, chlorine and fluorine atoms, $C_1$–$C_6$ alkyl radicals, optionally substituted by at least one radical chosen from hydroxyl, $C_1$–$C_4$ alkoxy, $C_2$–$C_4$ (poly)hydroxyalkoxy, amino, (di)($C_1$–$C_4$)alkylamino, $C_2$–$C_4$ (poly)hydroxyalkylamino, carboxyl, sulpho, $C_1$–$C_4$ alkoxycarbonyl and $C_1$–$C_4$ alkylthio radicals; and by at least one phenyl radical, optionally substituted by at least one radical chosen from hydroxyl, $C_1$–$C_2$ alkoxy, amino, (di)($C_1$–$C_2$)alkylamino, carboxyl, sulpho, $C_1$–$C_4$ alkyl, halogen, and $C_1$–$C_2$ alkylthio radicals,
- $R_1$, $R_2$, $R_9$ and $R_{12}$, which may be identical or different, are chosen from phenyl radicals which may be optionally substituted and $C_1$–$C_8$ alkyl radicals which may be optionally substituted by at least one radical chosen from hydroxyl, $C_1$–$C_2$ alkoxy, $C_2$–$C_4$ (poly)hydroxyalkoxy, amino, and (di)($C_1$–$C_2$)alkylamino radicals,
- $R_5$, $R_6$, $R_7$ and $R_8$, which may be identical or different, are chosen from a hydrogen atom; a chlorine atom; a bromine atom; linear and branched, saturated and unsaturated $C_1$–$C_8$ hydrocarbonaceous chains which can form at least one 3- to 6-membered carbonaceous ring, at least one of the carbon atoms of the carbonaceous chain of which can be replaced by at least one entity chosen from oxygen, nitrogen, and sulphur atoms and $SO_2$ groups, and the carbon atoms of which, independently of one another, can be substituted by at least one halogen atom; with the proviso that $R_5$, $R_6$, $R_7$, and $R_8$ do not comprise a peroxide bond or a diazo or nitroso radical,
- $R_3$, $R_4$, $R_{10}$, $R_{11}$, $R_{13}$, $R_{14}$ and $R_{15}$, which may be identical or different, are chosen from a hydrogen atom and linear and branched, saturated and unsaturated $C_1$–$C_{16}$, for example, $C_1$–$C_8$, hydrocarbonaceous chains which can form at least one 3- to 6-membered carbonaceous ring, at least one carbon atom of the carbonaceous chain of which can be replaced by at least one entity chosen from oxygen, nitrogen and sulphur atoms and $SO_2$ groups, and the carbon atoms of which, independently of one another, can be substituted by at least one halogen atom; with the proviso that $R_3$, $R_4$, $R_{10}$, $R_{11}$, $R_{13}$, $R_{14}$ and $R_{15}$ do not comprise a peroxide bond or a diazo or nitroso radical,
- $R_{14}$ with $R_{15}$ can form a carbonaceous aromatic ring, such as a phenyl.

The dyes of formula (I) can be obtained from known preparation processes disclosed, for example, in the documents DE-19 721619 or U.S. Pat. No. 5,852,179.

The following examples serve to illustrate the disclosure without, however, exhibiting a limiting nature.

EXAMPLE 1

The preparation of the dye was carried out in accordance with the disclosure of following formula:

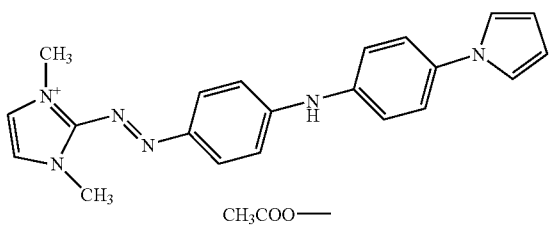

2-(4-amino-N-(4-(N-pyrrolophenyl))phenylazo)-1,3-dimethyl-3H-imidazol-1-ium acetate 1 g (2.9 mmol) of 2-(4-amino-N-(4-aminophenyl)phenylazo)-1,3-dimethyl-3H-imidazol-1-ium chloride and 100 ml of ethanol were charged to a fully equipped round-bottomed flask. 1 ml of dimethoxytetrahydrofuran (7.7 mmol) and 4 ml of acetic acid were added to the reaction medium. The mixture was brought to 80° C. for 35 minutes. It was allowed to return to ambient temperature with stirring. The reaction medium was poured into 100 ml of diisopropyl ether. After filtering through a sintered glass funnel and drying under vacuum at 30° C., 0.75 g of 2-(4-amino-N-(4-(N-pyrrolophenyl))phenylazo)-1,3-dimethyl-3H-imidazol-1-ium acetate was recovered in the form of a purple powder with a yield of 62%.

The visible light absorption characteristics of this dye were as follows:
$\lambda_{max}$=527 nm (EtOH)
$\epsilon$=50 000
Analyses:
  Mass ESI+: m/z=357 [M$^+$].
  $^1$H NMR: (400 MHz, CD$_3$OD): 2.01 ppm, 3H, CH$_3$ 4.07 ppm, 6H, 2×CH$_3$ 6.29 ppm, 2H, pyrrole 7.17 ppm, 4H, aromatic 7.39 ppm, 2H, aromatic 7.53 ppm, 2H, aromatic 7.60 ppm, 2H, imidazole 8.02 ppm, 2H, pyrrole.

EXAMPLE 2

The preparation the dye was carried out in accordance with the disclosure of following formula:

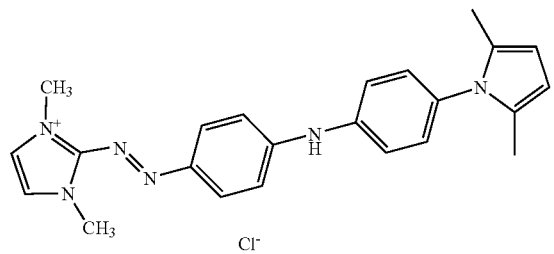

2-(4-amino-N-(4-(N-(2,5-dimethyl)pyrrolophenyl))phenylazo)-1,3-dimethyl-3H-imidazol-1-ium chloride 2-(4-amino-N-(4-aminophenyl)phenylazo)-1,3-dimethyl-3H-imidazol-1-ium chloride (0.75 g, 2.2 mmol) was dissolved in anhydrous ethanol (100 ml) in a round-bottomed flask equipped with a distillation column; 2,5-hexanedione (0.32 ml, 1.2 eq) and a catalytic amount of para-toluenesulfonic acid (4 mg, 1 catalytic %) were added. The reaction medium was brought to 130° C. for 5 hours while anhydrous ethanol was added during the distillation in order not to dry out the reaction medium.

Once the reaction was complete, the mixture was allowed to return to ambient temperature.

The reaction medium was poured into 100 ml of diisopropyl ether. After filtering through a sintered glass funnel and drying under vacuum at 30° C., 0.91 g of 2-(4-amino-N-(4-(N-(2,5-dimethyl)pyrrolophenyl))phenylazo)-1,3-dimethyl-3H-imidazol-1-ium chloride was recovered in the form of a purple powder with a yield of 98%.

The visible light absorption characteristics of this product were as follows:
$\lambda_{max}$=527 nm (EtOH)
$\epsilon$=52 300
Analyses:
  Mass ESI+: m/z=385 [M$^+$].
  $^1$H NMR: (400 MHz, CD$_3$OD): 2.02 ppm, 6H, 2×CH$_3$ 4.07 ppm, 6H, 2×CH$_3$ 5.80 ppm, 2H, pyrrole 7.23 ppm, 4H, aromatic 7.42 ppm, 2H, aromatic 7.59 ppm, 2H, imidazole 8.02 ppm, 2H, aromatic.

EXAMPLE 3

The preparation of the dye was carried out in accordance with the disclosure of following formula:

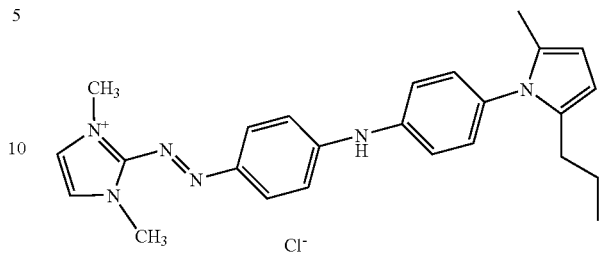

2-(4-amino-N-(4-(N-(2-methyl-5-propyl)pyrrolophenyl))phenylazo)-1,3-dimethyl-3H-imidazol-1-ium chloride 2-(4-amino-N-(4-aminophenyl)phenylazo)-1,3-dimethyl-3H-imidazol-1-ium chloride (0.75 g, 2.2 mmol) was dissolved in anhydrous ethanol (100 ml) in a round-bottomed flask equipped with a distillation column; 2,5-octanedione (0.4 g, 1.2 eq) and a catalytic amount of para-toluenesulfonic acid (4 mg, 1 catalytic %) were added. The reaction medium was brought to 130° C. for 5 hours while anhydrous ethanol was added during the distillation in order not to dry out the reaction medium.

Once the reaction was complete, the mixture was allowed to return to ambient temperature.

The reaction medium was poured into 100 ml of diisopropyl ether. After filtering through a sintered glass funnel and drying under vacuum at 30° C., 0.5 g of 2-(4-amino-N-(4-(N-(2-methyl-5-propyl)pyrrolophenyl))phenylazo)-1,3-dimethyl-3H-imidazol-1-ium chloride was recovered in the form of a purple powder with a yield of 51%.

The visible light absorption characteristics of this product were as follows:
$\lambda_{max}$=528 nm (EtOH)
$\epsilon$=53 900
Analyses:
  Mass ESI+: m/z=413 [M$^+$].
  $^1$H NMR: (400 MHz, CD$_3$OD): 0.82 ppm, 3H, CH$_3$ 1.43 ppm, 2H, CH$_2$ 1.99 ppm, 3H, CH$_3$ 2.33 ppm, 2H, CH$_2$ 4.07 ppm, 6H, 2×CH$_3$ 5.81 ppm, 2H, pyrrole 7.23 ppm, 4H, aromatic 7.42 ppm, 2H, aromatic 7.59 ppm, 2H, imidazole 8.02 ppm, 2H, aromatic.

EXAMPLE 4

The preparation of the dye was carried out in accordance with the disclosure of following formula:

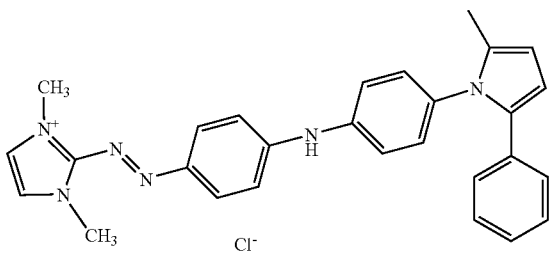

2-(4-amino-N-(4-(N-(2-methyl-5-phenyl)pyrrolophenyl))phenylazo)-1,3-dimethyl-3H-imidazol-1-ium chloride 2-(4-amino-N-(4-aminophenyl)phenylazo)-1,3-dimethyl-3H-imidazol-1-ium chloride (0.75 g, 2.2 mmol) was dissolved in anhydrous ethanol (100 ml) in a round-bottomed flask equipped with a distillation column; 1-phenyl-1,4-pentanedione (0.46 g, 1.2 eq.) and a catalytic amount of para-toluenesulfonic acid (4 mg, 1 catalytic %) were added. The reaction medium was brought to 130° C. for 5 hours while anhydrous ethanol was added during the distillation in order not to dry out the reaction medium.

Once the reaction was complete, the mixture was allowed to return to ambient temperature.

The reaction medium was poured into 100 ml of diisopropyl ether. After filtering through a sintered glass funnel and drying under vacuum at 30° C., 0.8 g of 2-(4-amino-N-(4-(N-(2-methyl-5-phenyl)pyrrolophenyl))phenylazo)-1,3-dimethyl-3H-imidazol-1-ium chloride was recovered in the form of a purple powder with a yield of 76%.

The visible light absorption characteristics of this product were as follows:
$\lambda_{max}$=530 nm (EtOH)
$\epsilon$=55 190
Analyses:
Mass ESI+: m/z=483 [M$^+$].
$^1$H NMR: (400 MHz, CD$_3$OD): 2.13 ppm, 3H, CH$_3$ 4.05 ppm, 6H, 2×CH$_3$ 6.01 ppm, 1H, pyrrole 6.25 ppm, 1H, pyrrole 7.30–7.04 ppm, 9H, aromatic 7.31 ppm, 2H, aromatic 7.58 ppm, 2H, imidazole 7.98 ppm, 2H, aromatic.

EXAMPLE 5

The preparation of the dye was carried out in accordance with the disclosure of following formula:

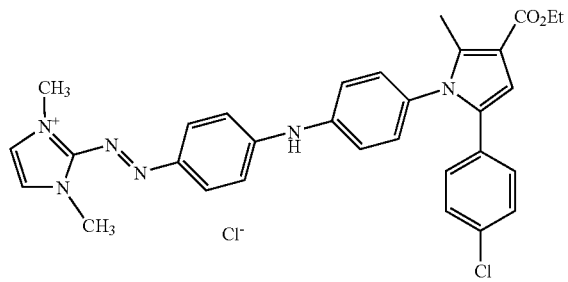

2-(4-amino-N-(4-(N-[2-methyl-3-carboxyethyl-5-(4-chlorophenyl)pyrrolophenyl)]phenylazo)-1,3-dimethyl-3H-imidazol-1-ium chloride 2-(4-amino-N-(4-aminophenyl)phenylazo)-1,3-dimethyl-3H-imidazol-1-ium chloride (0.75 g, 2.2 mmol) was dissolved in anhydrous ethanol (100 ml) in a round-bottomed flask equipped with a distillation column; 1-phenyl-1,4-pentanedione (0.46 g, 1.2 eq) and a catalytic amount of para-toluenesulfonic acid (4 mg, 1 catalytic %) were added. The reaction medium was brought to 130° C. for 5 hours while anhydrous ethanol was added as the distillation was carried out in order not to dry out the reaction medium.

Once the reaction was complete, the mixture was allowed to return to ambient temperature.

The reaction medium was poured into 100 ml of diisopropyl ether. After filtering through a sintered glass funnel and drying under vacuum at 30° C., 1.3 g of 2-(4-amino-N-(4-(N-[2-methyl-3-carboxyethyl-5-(4-chlorophenyl) pyrrolo phenyl)]phenylazo)-1,3-dimethyl-3H-imidazol-1-ium chloride was recovered in the form of a purple powder with a yield of 99%.

The visible light absorption characteristics of this product were as follows:

$\lambda_{max}$=525 nm (EtOH)
$\epsilon$=52 000
Analyses:
Mass ESI+: m/z=554 [M$^+$].
$^1$H NMR: (400 MHz, CD$_3$OD): 1.36 ppm, 3H, CH$_3$ (ester functional group) 2.40 ppm, 3H, CH$_3$ 4.07 ppm, 6H, 2×CH$_3$ 4.28 ppm, 2H, CH$_2$ (ester functional group) 6.74 ppm, 1H, pyrrole 7.07 ppm, 2H, aromatic 7.23–7.16 ppm, 6H, aromatic 7.37 ppm, 2H, aromatic 7.60 ppm, 2H, imidazole 8.02 ppm, 2H, aromatic.

DYEING EXAMPLES 6 TO 10

The 5 following lightening dyeing compositions were prepared immediately before use: (amounts expressed in grams of active material (AM))

|  | EXAMPLE | | | | |
| --- | --- | --- | --- | --- | --- |
|  | 6 | 7 | 8 | 9 | 10 |
| Dye of formula (I) according to the invention of Examples 1 to 5 | Dye Example 1 0.3 | Dye Example 2 0.2 | Dye Example 3 0.2 | Dye Example 4 0.2 | Dye Example 5 0.3 |
| Hydroxyethylcellulose | 0.768 | 0.768 | 0.768 | 0.768 | 0.768 |
| Nonionic surfactant: (C$_8$/C$_{10}$ 50/50)alkyl polyglucoside at 60% in aqueous solution | 6 | 6 | 6 | 6 | 6 |
| Benzyl alcohol | 8 | 8 | 8 | 8 | 8 |
| Polyethylene glycol (8 EO) | 12 | 12 | 12 | 12 | 12 |
| Aqueous ammonia solution, q.s. pH | 9 | 9 | 9 | 9 | 9 |
| Preservatives | q.s. | q.s. | q.s. | q.s. | q.s. |
| Demineralized water, q.s. for | 100 | 100 | 100 | 100 | 100 |

Immediately before use, one part by weight of each of these dyeing compositions was mixed with one part by weight of 40-volumes hydrogen peroxide. Each of these compositions was then applied to locks of natural hair comprising 90% white hairs.

The compositions were allowed to act at ambient temperature (approximately 20° C.) for 30 minutes and then the locks were rinsed with water, washed with a shampoo and then dried.

The colour obtained was evaluated in the Munsell colouring system.

The hues obtained have been listed in the table below.

|  | Munsell values | |
| --- | --- | --- |
|  | Hue Value/Chroma | Highlight |
| Example 6 | 3.9 RP 2.1/2.0 | Purple |
| Example 7 | 4.7 RP 2.3/3.0 | Purple |
| Example 8 | 6.4 RP 2.3/3.5 | Purple |
| Example 9 | 6.5 RP 2.5/3.8 | Purple |
| Example 10 | 9.4 RP 2.7/5.1 | Purple |

What is claimed is:

1. A composition for dyeing human keratinous fibres comprising, in a cosmetically acceptable medium, at least one monocationic monoazo dye of formula (I):

$$W_1-N=N=W_2-NW_3-W_4-W_5 \quad (I)$$

wherein:

$W_1$ is chosen from 5- and 6-membered cationic aromatic heterocycles of formulae (II) and (III):

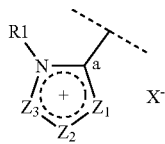

Formula (II)

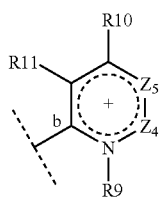

Formula (III)

wherein:
- $Z_1$ is chosen from an oxygen atom, a sulphur atom, $NR_2$ radicals, and $CR_3$ radicals,
- $Z_2$ is chosen from a nitrogen atom and $CR_4$ radicals,
- $Z_3$ is chosen from $NR_{12}$ radicals and $CR_{13}$ radicals,
- $Z_4$ is chosen from a nitrogen atom and $CR_{14}$ radicals,
- $Z_5$ is chosen from a nitrogen atom and $CR_{15}$ radicals,
- with the proviso that formulae (II) and (III) do not comprise more than two adjacent heteroatoms;
- the bond a connects the 5-membered cationic ring of formula (II) to the azo functional group of formula (I),
- the bond b connects the 6-membered cationic ring of formula (III) to the azo functional group of formula (I),
- $X^-$ is chosen from organic and inorganic anions,
- $W_2$ and $W_4$ (formula I), which may be identical or different, are chosen from divalent carbonaceous aromatic groups and pyridine groups of formulae (IV) and (V):

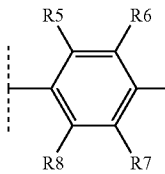

Formula (IV)

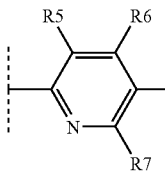

Formula (V)

$W_3$ is chosen from a hydrogen atom and $C_1$–$C_6$ alkyl radicals that may be optionally substituted with at least one radical chosen from hydroxyl radicals, alkoxy radicals, amino radicals, mono($C_1$–$C_4$)alkylamino radicals, and di($C_1$–$C_4$)alkylamino radicals, $W_5$ is a 5-membered nitrogenous heteroaromatic radical connected to $W_4$ via the nitrogen atom of the ring of the said heteroaromatic radical, wherein the heteroaromatic radical is chosen from pyrazolyl, pyrrolyl, imidazolyl, triazolyl, and thiadiazolyl radicals, it being possible for each of these heteroaromatic radicals to be substituted by at least one entity chosen from hydrogen, chlorine, and fluorine atoms, $C_1$–$C_6$ alkyl radicals optionally substituted by at least one radical chosen from hydroxyl, $C_1$–$C_4$ alkoxy, $C_2$–$C_4$ (poly) hydroxyalkoxy, amino, (di)($C_1$–$C_4$)alkylamino, $C_2$–$C_4$ (poly)hydroxyalkylamino, carboxyl, sulpho, $C_1$–$C_4$ alkoxycarbonyl, and $C_1$–$C_4$ alkylthio radicals; and at least one phenyl radical, which may be optionally substituted by at least one entity chosen from halogen atoms and hydroxyl, $C_1$–$C_2$ alkoxy, amino, (di)($C_1$–$C_2$) alkylamino, carboxyl, sulpho, $C_1$–$C_4$ alkyl, and $C_1$–$C_2$ alkylthio radicals, $R_1$, $R_2$, $R_9$ and $R_{12}$, which may be identical or different, are chosen from phenyl radicals that may be optionally substituted and $C_1$–$C_8$ alkyl radicals that may be optionally substituted by at least one radical chosen from hydroxyl, $C_1$–$C_2$ alkoxy, $C_2$–$C_4$ (poly) hydroxyalkoxy, amino, and (di)($C_1$–$C_2$)alkylamino radicals, $R_5$, $R_6$, $R_7$ and $R_8$, which may be identical or different, are chosen from a hydrogen atom; a chlorine atom; a bromine atom; linear and branched, saturated and unsaturated $C_1$–$C_8$ hydrocarbonaceous chains that can form at least one 3- to 6-membered carbonaceous ring, at least one carbon atom of the carbonaceous chain of which can be replaced by at least one entity chosen from oxygen, nitrogen, and sulphur atoms and $SO_2$ groups, and the carbon atoms of which can, independently of one another, be substituted by at least one halogen atom; with the proviso that $R_5$, $R_6$, $R_7$ and $R_8$ do not comprise a peroxide bond or a diazo or nitroso radical, $R_3$, $R_4$, $R_{10}$, $R_{11}$, $R_{13}$, $R_{14}$ and $R_{15}$, which may be identical or different, are chosen from a hydrogen atom and linear and branched, saturated and unsaturated $C_1$–$C_{16}$ hydrocarbonaceous chains that can form at least one 3- to 6-membered carbonaceous ring, one or more carbon atoms of the carbonaceous chain of which can be replaced by at least one entity chosen from oxygen, nitrogen, and sulphur atoms, and $SO_2$ groups, and the carbon atoms of which can, independently of one another, be substituted by at least one halogen atom; with the proviso that $R_3$, $R_4$, $R_{10}$, $R_{11}$, $R_{13}$, $R_{14}$ and $R_{15}$ do not comprise a peroxide bond or a diazo or nitroso radical, $R_4$ with $R_{13}$ and $R_{14}$ with $R_{15}$ can form a carbonaceous aromatic ring.

2. The composition according to claim 1, wherein the human keratinous fibers are human hair.

3. The composition according to claim 1, wherein $R_4$ with $R_{13}$ and $R_{14}$ with $R_{15}$ form a phenyl ring.

4. The composition according to claim 1, wherein $W_3$ (formula I) is chosen from a hydrogen atom and $C_1$–$C_4$ alkyl radicals that may be optionally substituted with at least one radical chosen from hydroxyl, $C_1$–$C_2$ alkoxy, amino, and (di)($C_1$–$C_2$)alkylamino radicals.

5. The composition according to claim 4, wherein $W_3$ (formula I) is chosen from a hydrogen atom and methyl, ethyl, and 2-hydroxyethyl radicals.

6. The composition according to claim 5, wherein $W_3$ (formula I) is a hydrogen atom.

7. The composition according to claim 1, wherein $W_5$ (formula I) is chosen from pyrazolyl, pyrrolyl, and imidazolyl rings.

8. The composition according to claim 7, wherein $W_5$ (formula I) is chosen from pyrrolyl and imidazolyl rings.

9. The composition according to claim 8, wherein $W_5$ (formula I) is a 5-membered nitrogenous heteroaromatic ring substituted with at least one radical chosen from $C_1$–$C_6$ alkyl radicals that may be optionally substituted by at least one entity chosen from hydroxyl, $C_1$–$C_4$ alkoxy, amino, $C_1$–$C_4$ monoalkylamino, $C_1$–$C_4$ alcoxycarbonyl and di($C_1$–$C_4$)alkylamino radicals; chlorine and fluorine atoms; phenyl radicals that may be optionally substituted with at least one entity chosen from a bromine atom, a chlorine atom, and hydroxyl, $C_1$–$C_2$ alkoxy, amino, (di)($C_1$–$C_2$) alkylamino, di($C_1$–$C_2$)alkylamino, and $C_1$–$C_2$ alkoxy radicals.

10. The composition according to claim 8, wherein $W_5$ (formula I) is chosen from pyrrolyl and imidazolyl radicals optionally substituted with one or two radicals chosen from methyl, ethyl, propyl, phenyl, 4-chlorophenyl and ethoxycarbonyl radicals.

11. The composition according to claim 1, wherein $R_1$, $R_2$, $R_9$ and $R_{12}$, which may be identical or different, are chosen from $C_1$–$C_4$ alkyl radicals optionally substituted with at least one radical chosen from hydroxyl, $C_1$–$C_2$ alkoxy, amino, and (di)($C_1$–$C_2$)alkylamino radicals.

12. The composition according to claim 11, wherein $R_1$, $R_2$, $R_9$ and $R_{12}$, which may be identical or different, are chosen from methyl, ethyl, propyl, and 2-hydroxyethyl radicals.

13. The composition according to claim 1, wherein $R_5$, $R_6$, $R_7$ and $R_8$, which may be identical or different, are chosen from a hydrogen atom and methyl, ethyl, isopropyl, methoxymethyl, hydroxymethyl, 1-carboxymethyl, 1-aminomethyl, 2-carboxyethyl, 2-hydroxyethyl, 3-hydroxypropyl, 1,2-dihydroxyethyl, 1-hydroxy-2-aminoethyl, 2-hydroxy-1-aminoethyl, methoxy, ethoxy, 2-hydroxyethyloxy, and 2-aminoethyloxy radicals.

14. The composition according to claim 13, wherein $R_5$, $R_6$, $R_7$ and $R_8$, which may be identical or different, are chosen from a hydrogen atom and methyl, hydroxymethyl, 2-hydroxyethyl, 1,2-dihydroxyethyl, methoxy, and 2-hydroxyethyloxy radicals.

15. The composition according to claim 14, wherein $R_5$, $R_6$, $R_7$ and $R_8$, which may be identical or different, are chosen from a hydrogen atom, methyl radicals and methoxy radicals.

16. The composition according to claim 1, wherein $R_3$, $R_4$, $R_{10}$, $R_{11}$, $R_{13}$, $R_{14}$ and $R_{15}$, which may be identical or different, are chosen from hydrogen atoms; linear and branched $C_1$–$C_4$ alkyl radicals optionally substituted by at least one radical chosen from hydroxyl, $C_1$–$C_2$ alkoxy, $C_2$–$C_4$ (poly)hydroxyalkoxy, amino and (di)($C_1$–$C_2$) alkylamino radicals; phenyl radicals optionally substituted by at least one entity chosen from hydroxyl, $C_1$–$C_2$ alkoxy, $C_2$–$C_4$ (poly)hydroxyalkoxy, amino and (di)($C_1$–$C_2$) alkylamino radicals, and halogen atoms; sulphonylamino radicals; $C_1$–$C_2$ alkoxy radicals; $C_2$–$C_4$ (poly) hydroxyalkoxy radicals; amino radicals; (di)($C_1$–$C_2$) alkylamino radicals; and $C_2$–$C_4$ (poly)hydroxyalkylamino radicals.

17. The composition according to claim 16, wherein the halogen atoms are chosen from chlorine, fluorine and bromine atoms.

18. The composition according to claim 16, wherein $R_3$, $R_4$, $R_{10}$, $R_{11}$, $R_{13}$, $R_{14}$ and $R_{15}$, which may be identical or different, are chosen from a hydrogen atom; $C_1$–$C_4$ alkyl radicals optionally substituted by at least one radical chosen from hydroxyl, amino and (di)($C_1$–$C_2$)alkylamino radicals; $C_1$–$C_2$ alkoxy radicals; amino radicals; (di)($C_1$–$C_2$) alkylamino radicals; and $C_2$–$C_4$ (poly)hydroxyalkylamino radicals.

19. The composition according to claim 18, wherein $R_3$, $R_4$, $R_{10}$, $R_{11}$, $R_{13}$, $R_{14}$ and $R_{15}$, which may be identical or different, are chosen from a hydrogen atom and methyl, phenyl, 2-hydroxymethyl, methoxy, ethoxy, 2-hydroxyethyloxy, amino, methylamino, dimethylamino and 2-hydroxyethylamino radicals.

20. The composition according to claim 1, wherein $Z_1$ (formula (II)) is chosen from $NR_2$ radicals.

21. The composition according to claim 1, wherein $Z_2$ (formula (II)) is chosen from $CR_4$ radicals.

22. The composition according to claim 1, wherein $Z_3$ (formula (II)) is chosen from $CR_{13}$ radicals.

23. The composition according to claim 1, wherein $Z_4$ (formula (III)) is chosen from $CR_{14}$ radicals.

24. The composition according to claim 1, wherein $Z_5$ (formula (III)) is chosen from $CR_{15}$.

25. The composition according to claim 1, wherein the monocationic monoazo dye of formula (I) is chosen from:

2-(4-amino-N-(4-(N-pyrrolophenyl))phenylazo)-1,3-dimethyl-3H-imidazol-1-ium, 2-(4-amino-N-(4-(N-(2,5-di-methyl)pyrrolophenyl)) phenylazo)-1,3-dimethyl-3H-imidazol-1-ium, 2-(4-amino-N-(4-(N-(2-methyl-5-propyl)pyrrolophenyl)) phenylazo)-1,3-dimethyl-3H-imidazol-1-ium, 2-(4-amino-N-(4-(N-(2-methyl-5-phenyl)pyrrolophenyl)) phenylazo)-1,3-dimethyl-3H-imidazol-1-ium, and 2-(4-amino-N-(4-(N-[2-methyl-3-carboxyethyl-5-(4-chlorophenyl)pyrrolophenyl)]phenylazo)-1,3-dimethyl-3H-imidazol-1-ium, wherein each of these dyes is associated with at least one $X^-$ anion.

26. The composition according to claim 1, wherein $X^-$ is chosen from halides, hydroxides, sulphates, hydrogensulphates, ($C_1$–$C_6$)alkyl sulphates, acetates, tartrates, oxalates, ($C_1$–$C_6$)alkylsulphonates and arylsulphonates, which are optionally substituted by at least one $C_1$–$C_4$ alkyl radical.

27. The composition according to claim 1, wherein the monocationic monoazo dye of formula (I) is present in an amount ranging from 0.001 to 5% by weight, relative to the total weight of the dyeing composition.

28. The composition according to claim 27, wherein the monocationic monoazo dye of formula (I) is present in an amount ranging from 0.05 to 2% by weight, relative to the total weight of the composition.

29. The composition according to claims 1, further comprising at least one direct dye other than those of formula (I), wherein said at least one direct dye is chosen from neutral, acidic and cationic direct nitrobenzene dyes; neutral, acidic and cationic direct azo dyes; neutral, acidic and cationic direct quinone dyes; direct azine dyes; direct methine dyes; direct triarylmethane dyes, direct indoamine dyes, and direct natural dyes.

30. The composition according to claim 29, wherein the cationic direct quinone dyes are chosen from anthraquinone dyes.

31. The composition according to claim 1, further comprising at least one oxidizing agent.

32. The composition according to claim 1, wherein the at least one oxidizing agent is hydrogen peroxide.

33. The composition according to claim 1, further comprising at least one oxidation base.

34. The composition according to claim 33, wherein the at least one oxidation base is chosen from para-phenylenediamines, bisphenylalkylenediamines, para-aminophenols, ortho-aminophenols, heterocyclic bases and their addition salts with an acid.

35. The composition according to claim 33, further comprising at least one coupler.

36. The composition according to claim 35, wherein the at least one coupler is chosen from meta-phenylenediamines, meta-aminophenols, meta-diphenols, naphthalene couplers, heterocyclic couplers and their addition salts with an acid.

37. The composition according to claim 1, wherein $R_3$, $R_4$, $R_{10}$, $R_{11}$, $R_{13}$, $R_{14}$ and $R_{15}$, which may be identical or different, are chosen from hydrogen atoms; linear and branched $C_1$–$C_8$ alkyl radicals optionally substituted by at least one radical chosen from hydroxyl, $C_1$–$C_2$ alkoxy, $C_2$–$C_4$ (poly)hydroxyalkoxy, amino and (di)($C_1$–$C_2$) alkylamino radicals; phenyl radicals optionally substituted by at least one entity chosen from hydroxyl, $C_1$–$C_2$ alkoxy, $C_2$–$C_4$ (poly)hydroxyalkoxy, amino and (di)($C_1$–$C_2$) alkylamino radicals, and halogen atoms; sulphonylamino radicals; $C_1$–$C_2$ alkoxy radicals; $C_2$–$C_4$ (poly) hydroxyalkoxy radicals; amino radicals; (di)($C_1$–$C_2$) alkylamino radicals; and $C_2$–$C_4$ (poly)hydroxyalkylamino radicals.

38. The composition according to claim 1, wherein if $W_5$ is imidazole, $W_1$ is benzimidazole, and $W_4$ is phenyl, then $W_3$ not hydrogen.

39. A process for the direct dyeing of human keratinous fibres, comprising applying to the fibres a dyeing composition comprising, in a cosmetically acceptable medium, at least one monocationic monoazo dye of formula (I):

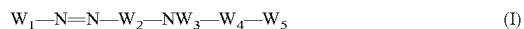

wherein:

$W_1$ is chosen from 5- and 6-membered cationic aromatic heterocycles of formulae (II) and (III):

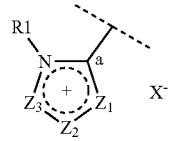

Formula (II)

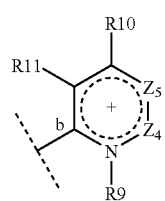

Formula (III)

wherein:

$Z_1$ is chosen from an oxygen atom, a sulphur atom, $NR_2$ radicals, and $CR_3$ radicals, $Z_2$ is chosen from a nitrogen atom and $CR_4$ radicals, $Z_3$ is chosen from $NR_{12}$ radicals and $CR_{13}$ radicals, $Z_4$ is chosen from a nitrogen atom and $CR_{14}$ radicals, $Z_5$ is chosen from a nitrogen atom and $CR_{15}$ radicals, with the proviso that formulae (II) and (III) do not comprise more than two adjacent heteroatoms;

the bond a connects the 5-membered cationic ring of formula (II) to the azo functional group of formula (I), the bond b connects the 6-membered cationic ring of formula (III) to the azo functional group of formula (I), $X^-$ is chosen from organic and inorganic anions, $W_2$ and $W_4$ (formula I), which may be identical or different, are chosen from divalent carbonaceous aromatic groups and pyridine groups of formulae (IV) and (V):

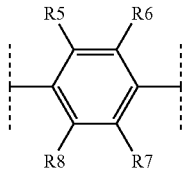

Formula (IV)

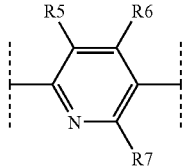

Formula (V)

$W_3$ is chosen from a hydrogen atom and $C_1$–$C_6$ alkyl radicals that may be optionally substituted with at least one radical chosen from hydroxyl radicals, alkoxy radicals, amino radicals, mono($C_1$–$C_4$)alkylamino radicals, and di($C_1$–$C_4$)alkylamino radicals, $W_5$ is a 5-membered nitrogenous heteroaromatic radical connected to $W_4$ via the nitrogen atom of the ring of the said heteroaromatic radical, wherein the heteroaromatic radicals are chosen from pyrazolyl, pyrrolyl, imidazolyl, triazolyl, and thiadiazolyl radicals, it being possible for each of these heteroaromatic radicals to be substituted by at least one entity chosen from hydrogen, chlorine, and fluorine atoms, $C_1$–$C_6$ alkyl radicals optionally substituted by at least one radical chosen from hydroxyl, $C_1$–$C_4$ alkoxy, $C_2$–$C_4$ (poly) hydroxyalkoxy, amino, (di)($C_1$–$C_4$)alkylamino, $C_2$–$C_4$ (poly)hydroxyalkylamino, carboxyl, sulpho, $C_1$–$C_4$ alkoxycarbonyl, and $C_1$–$C_4$ alkylthio radicals; and at least one phenyl radical, which may be optionally substituted by at least one entity chosen from halogen atoms and hydroxyl, $C_1$–$C_2$ alkoxy, amino, (di)($C_1$–$C_2$) alkylamino, carboxyl, sulpho, $C_1$–$C_4$ alkyl, and $C_1$–$C_2$ alkylthio radicals, $R_1$, $R_2$, $R_9$ and $R_{12}$, which may be identical or different, are chosen from phenyl radicals that may be optionally substituted and $C_1$–$C_8$ alkyl radicals that may be optionally substituted by at least one radical chosen from hydroxyl, $C_1$–$C_2$ alkoxy, $C_2$–$C_4$ (poly) hydroxyalkoxy, amino, and (di)($C_1$–$C_2$)alkylamino radicals, $R_5$, $R_6$, $R_7$ and $R_8$, which may be identical or different, are chosen from a hydrogen atom; a chlorine atom; a bromine atom; linear and branched, saturated and unsaturated $C_1$–$C_8$ hydrocarbonaceous chains that can form at least one 3- to 6-membered carbonaceous ring, at least one carbon atom of the carbonaceous chain of which can be replaced by at least one entity chosen from oxygen, nitrogen, and sulphur atoms and $SO_2$ groups, and the carbon atoms of which can, independently of one another, be substituted by at least one halogen atom; with the proviso that $R_5$, $R_6$, $R_7$ and $R_8$ do not comprise a peroxide bond or a diazo or nitroso radical, $R_3$, $R_4$, $R_{10}$, $R_{11}$, $R_{13}$, $R_{14}$ and $R_{15}$, which may be identical or different, are chosen from a hydrogen atom and linear and branched, saturated and unsaturated $C_1$–$C_{16}$ hydrocarbonaceous chains that can form at least one 3- to 6-membered carbonaceous ring, one or more carbon atoms of the carbonaceous chain of which can be replaced by at least one entity chosen from oxygen, nitrogen, and sulphur atoms, and $SO_2$ groups, and the carbon atoms of which can, independently of one another, be substituted by at least one halogen atom; with the proviso that $R_3$, $R_4$, $R_{10}$, $R_{11}$, $R_{13}$, $R_{14}$ and $R_{15}$ do not comprise a peroxide bond or diazo or nitroso radicals, $R_4$ with $R_{13}$ and $R_{14}$ with $R_{15}$ can form a carbonaceous aromatic ring.

40. The process according to claim 39, wherein the human keratinous fibers are hair.

41. The process according to claim 39, wherein the dyeing composition further comprises at least one oxidizing agent.

42. The process according to claim 41, wherein the at least one oxidizing agent is mixed at the time of use with the dyeing composition.

43. The process according to claim 41, wherein the at least one oxidizing agent is applied to the fibres in the form of an oxidizing composition, simultaneously with, or sequentially to, the dyeing composition.

44. The process according to claim 39, wherein if $W_5$ is imidazole, $W_1$ is benzimidazole, and $W_4$ is phenyl, then $W_3$ is not hydrogen.

45. A monocationic monoazo compound chosen from compounds of formula (I):

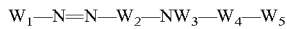
(I)

wherein:

$W_1$ is chosen from 5- and 6-membered cationic aromatic heterocycles of formulae (II) and (III):

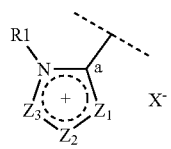
Formula (II)

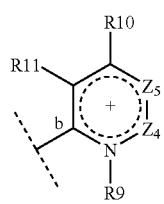
Formula (III)

wherein:

$Z_1$ is chosen from an oxygen atom, a sulphur atom, $NR_2$ radicals, and $CR_3$ radicals, $Z_2$ is chosen from a nitrogen atom and $CR_4$ radicals, $Z_3$ is chosen from $NR_{12}$ radicals and $CR_{13}$ radicals, $Z_4$ is chosen from a nitrogen atom and $CR_{14}$ radicals, $Z_5$ is chosen from a nitrogen atom and $CR_{15}$ radicals, with the proviso that formulae (II) and (III) do not comprise more than two adjacent heteroatoms;

the bond a connects the 5-membered cationic ring of formula (II) to the azo functional group of formula (I), the bond b connects the 6-membered cationic ring of formula (III) to the azo functional group of formula (I), $X^-$ is chosen from organic and inorganic anions, $W_2$ and $W_4$ (formula I), which may be identical or different, are chosen from divalent carbonaceous aromatic groups and pyridine groups of formulae (IV) and (V):

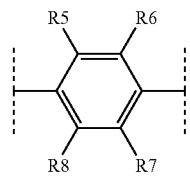
Formula (IV)

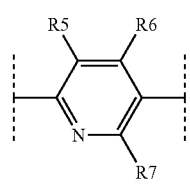
Formula (V)

$W_3$ is chosen from a hydrogen atom and $C_1$–$C_6$ alkyl radicals that may be optionally substituted with at least one radical chosen from hydroxyl radicals, alkoxy radicals, amino radicals, mono($C_1$–$C_4$)alkylamino radicals, and di($C_1$–$C_4$)alkylamino radicals, $W_5$ is a 5-membered nitrogenous heteroaromatic radical connected to $W_4$ via the nitrogen atom of the ring of the said heteroaromatic radical, wherein the heteroaromatic radicals are chosen from pyrazolyl, pyrrolyl, imidazolyl, triazolyl, and thiadiazolyl radicals, it being possible for each of these heteroaromatic radicals to be substituted by at least one entity chosen from hydrogen, chlorine, and fluorine atoms, $C_1$–$C_6$ alkyl radicals optionally substituted by at least one radical chosen from hydroxyl, $C_1$–$C_4$ alkoxy, $C_2$–$C_4$ (poly) hydroxyalkoxy, amino, (di)($C_1$–$C_4$)alkylamino, $C_2$–$C_4$ (poly)hydroxyalkylamino, carboxyl, sulpho, $C_1$–$C_4$ alkoxycarbonyl, and $C_1$–$C_4$ alkylthio radicals; and at least one phenyl radical, which may be optionally substituted by at least one entity chosen from halogen atoms and hydroxyl, $C_1$–$C_2$ alkoxy, amino, (di)($C_1$–$C_2$) alkylamino, carboxyl, sulpho, $C_1$–$C_4$ alkyl, and $C_1$–$C_2$ alkylthio radicals, $R_1$, $R_2$, $R_9$ and $R_{12}$, which may be identical or different, are chosen from phenyl radicals that may be optionally substituted and $C_1$–$C_8$ alkyl radicals that may be optionally substituted by at least one radical chosen from hydroxyl, $C_1$–$C_2$ alkoxy, $C_2$–$C_4$ (poly) hydroxyalkoxy, amino, and (di)($C_1$–$C_2$)alkylamino radicals, $R_5$, $R_6$, $R_7$ and $R_8$, which may be identical or different, are chosen from a hydrogen atom; a chlorine atom; a bromine atom; linear and branched, saturated and unsaturated $C_1$–$C_8$ hydrocarbonaceous chains that can form at least one 3- to 6-membered carbonaceous ring, at least one carbon atom of the carbonaceous chain of which can be replaced by at least one entity chosen from oxygen, nitrogen, and sulphur atoms and $SO_2$ groups, and the carbon atoms of which can, independently of one another, be substituted by at least one halogen atom; with the proviso that $R_5$, $R_6$, $R_7$ and $R_8$ do not comprise a peroxide bond or a diazo or nitroso radical, $R_3$, $R_4$, $R_{10}$, $R_{11}$, $R_{13}$, $R_{14}$ and $R_{15}$, which may be identical or different, are chosen from a hydrogen atom and linear and branched, saturated and unsaturated $C_1$–$C_{16}$ hydrocarbonaceous chains that can form at least one 3- to 6-membered carbonaceous ring, one or more carbon atoms of the carbonaceous chain of which can be replaced by at least one entity chosen from oxygen, nitrogen, and sulphur atoms, and $SO_2$ groups, and the carbon atoms of which can, independently of one another, be substituted by at least one halogen atom; with the proviso that $R_3$, $R_4$, $R_{10}$, $R_{11}$, $R_{13}$, $R_{14}$ and $R_{15}$ do not comprise a peroxide bond or diazo or nitroso radicals, $R_4$ with $R_{13}$ and $R_{14}$ with $R_{15}$ can form a carbonaceous aromatic ring.

46. The monocationic monoazo compound according to claim 45, wherein $R_3$, $R_4$, $R_{10}$, $R_{11}$, $R_{13}$, $R_{14}$ and $R_{15}$, which may be identical or different, are chosen from hydrogen atoms; linear and branched $C_1$–$C_8$ alkyl radicals optionally substituted by at least one radical chosen from hydroxyl, $C_1$–$C_2$ alkoxy, $C_2$–$C_4$ (poly)hydroxyalkoxy, amino and (di)($C_1$–$C_2$)alkylamino radicals; phenyl radicals optionally substituted by at least one entity chosen from hydroxyl, $C_1$–$C_2$ alkoxy, $C_2$–$C_4$ (poly)hydroxyalkoxy, amino and (di)($C_1$–$C_2$) alkylamino radicals, and halogen atoms; sulphonylamino radicals; $C_1$–$C_2$ alkoxy radicals; $C_2$–$C_4$ (poly)hydroxyalkoxy radicals; amino radicals; (di)($C_1$–$C_2$) alkylamino radicals; and $C_2$–$C_4$ (poly)hydroxyalkylamino radicals.

47. A multi-compartment kit or device for the dyeing of human keratinous fibres, comprising:
at least one first compartment comprises a composition comprising, in a cosmetically acceptable medium,
at least one monocationic monoazo dye of formula (I):

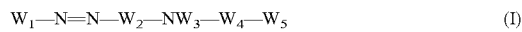  (I)

wherein:
$W_1$ is chosen from 5- and 6-membered cationic aromatic heterocycles of formulae (II) and (III):

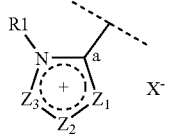

Formula (II)

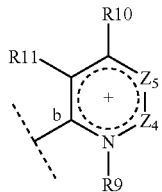

Formula (III)

wherein:
$Z_1$ is chosen from an oxygen atom, a sulphur atom, $NR_2$ radicals, and $CR_3$ radicals,
$Z_2$ is chosen from a nitrogen atom and $CR_4$ radicals,
$Z_3$ is chosen from $NR_{12}$ radicals and $CR_{13}$ radicals,
$Z_4$ is chosen from a nitrogen atom and $CR_{14}$ radicals,
$Z_5$ is chosen from a nitrogen atom and $CR_{15}$ radicals,
with the proviso that formulae (II) and (III) do not comprise more than two adjacent heteroatoms;

the bond a connects the 5-membered cationic ring of formula (II) to the azo functional group of formula (I),
the bond b connects the 6-membered cationic ring of formula (III) to the azo functional group of formula (I),
$X^-$ is chosen from organic and inorganic anions,
$W_2$ and $W_4$ (formula I), which may be identical or different, are chosen from divalent carbonaceous aromatic groups and pyridine groups of formulae (IV) and (V):

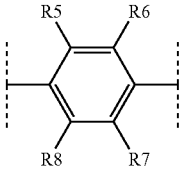

Formula (IV)

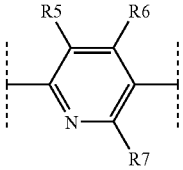

Formula (V)

$W_3$ is chosen from a hydrogen atom and $C_1$–$C_6$ alkyl radicals that may be optionally substituted with at least one radical chosen from hydroxyl radicals, alkoxy radicals, amino radicals, mono($C_1$–$C_4$)alkylamino radicals, and di($C_1$–$C_4$)alkylamino radicals, $W_5$ is a 5-membered nitrogenous heteroaromatic radical connected to $W_4$ via the nitrogen atom of the ring of the said heteroaromatic radical, wherein the heteroaromatic radicals are chosen from pyrazolyl, pyrrolyl, imidazolyl, triazolyl, and thiadiazolyl radicals, it being possible for each of these heteroaromatic radicals to be substituted by at least one entity chosen from hydrogen, chlorine, and fluorine atoms, $C_1$–$C_6$ alkyl radicals optionally substituted by at least one radical chosen from hydroxyl, $C_1$–$C_4$ alkoxy, $C_2$–$C_4$ (poly)hydroxyalkoxy, amino, (di)($C_1$–$C_4$)alkylamino, $C_2$–$C_4$ (poly)hydroxyalkylamino, carboxyl, sulpho, $C_1$–$C_4$ alkoxycarbonyl, and $C_1$–$C_4$ alkylthio radicals; and at least one phenyl radical, which may be optionally substituted by at least one entity chosen from halogen atoms and hydroxyl, $C_1$–$C_2$ alkoxy, amino, (di)($C_1$–$C_2$) alkylamino, carboxyl, sulpho, $C_1$–$C_4$ alkyl, and $C_1$–$C_2$ alkylthio radicals, $R_1$, $R_2$, $R_9$ and $R_{12}$, which may be identical or different, are chosen from phenyl radicals that may be optionally substituted and $C_1$–$C_8$ alkyl radicals that may be optionally substituted by at least one radical chosen from hydroxyl, $C_1$–$C_2$ alkoxy, $C_2$–$C_4$ (poly)hydroxyalkoxy, amino, and (di)($C_1$–$C_2$)alkylamino radicals, $R_5$, $R_6$, $R_7$ and $R_8$, which may be identical or different, are chosen from a hydrogen atom; a chlorine atom; a bromine atom; linear and branched, saturated and unsaturated $C_1$–$C_8$ hydrocarbonaceous chains that can form at least one 3- to 6-membered carbonaceous ring, at least one carbon atom of the carbonaceous chain of which can be replaced by at least one entity chosen from oxygen, nitrogen, and sulphur atoms and $SO_2$ groups, and the carbon atoms of which can, independently of one another, be substituted by at least one halogen atom; with the proviso that $R_5$, $R_6$, $R_7$ and $R_8$ do not comprise a peroxide bond or a diazo or nitroso radical, $R_3$, $R_4$, $R_{10}$, $R_{11}$, $R_{13}$, $R_{14}$ and $R_{15}$, which may be identical or different, are chosen from a hydrogen atom and linear and branched, saturated and unsaturated $C_1$–$C_{16}$ hydrocarbonaceous chains that can form at least one 3- to 6-membered carbonaceous ring, one or more carbon atoms of the carbonaceous chain of which can be replaced by at least one entity chosen from oxygen, nitrogen, and sulphur atoms, and $SO_2$ groups, and the carbon atoms of which can, independently of one another, be substituted by at least one halogen atom; with the proviso that $R_3$, $R_4$, $R_{10}$, $R_{11}$, $R_{13}$, $R_{14}$ and $R_{15}$ do not comprise a peroxide bond or a diazo or nitroso radical, $R_4$ with $R_{13}$ and $R_{14}$ with $R_{15}$ can form a carbonaceous aromatic ring; and at least one second compartment comprises at least one oxidizing composition.

* * * * *

UNITED STATES PATENT AND TRADEMARK OFFICE
CERTIFICATE OF CORRECTION

PATENT NO.         : 7,077,873 B2
APPLICATION NO.   : 10/658409
DATED              : July 18, 2006
INVENTOR(S)        : Hervé David et al.

It is certified that error appears in the above-identified patent and that said Letters Patent is hereby corrected as shown below:

On the title page, item (73), "L'Oréal, SA," should read --L'Oréal SA,--.

In claim 1, column 35, line 5, "$W_1$-N=N=$W_2$-N$W_3$-$W_4$-$W_5$" should read --$W_1$-N=N-$W_2$-N$W_3$-$W_4$-$W_5$--.

In claim 29, column 38, line 53, "claims" should read --claim--.

In claim 38, column 39, line 31, "$W_3$ not" should read --$W_3$ is not--.

Signed and Sealed this

Fifth Day of December, 2006

JON W. DUDAS
*Director of the United States Patent and Trademark Office*